(12) United States Patent
Brosch et al.

(10) Patent No.: US 8,398,991 B2
(45) Date of Patent: Mar. 19, 2013

(54) **MODIFIED ESAT-6 MOLECULES AND IMPROVED VACCINE STRAINS OF *MYCOBACTERIUM BOVIS* BCG**

(75) Inventors: Roland Brosch, Paris (FR); Priscille Brodin, Paris (FR); Stewart Cole, Clamart (FR); Laleh Majlessi, Montigny le Bretonneux (FR); Claude Leclerc, Paris (FR)

(73) Assignees: Institut Pasteur, Paris (FR); Institut Nationale de la Sante et de la Recherche Medicale, Paris (FX)

( * ) Notice: Subject to any disclaimer, the term of this patent is extended or adjusted under 35 U.S.C. 154(b) by 308 days.

(21) Appl. No.: 11/455,929

(22) Filed: Jun. 20, 2006

(65) Prior Publication Data

US 2007/0009547 A1    Jan. 11, 2007

Related U.S. Application Data

(60) Provisional application No. 60/692,561, filed on Jun. 22, 2005.

(51) Int. Cl.
*A61K 39/02* (2006.01)
(52) U.S. Cl. .................................................. 424/200.1
(58) Field of Classification Search ........................ None
See application file for complete search history.

(56) References Cited

U.S. PATENT DOCUMENTS 5,731,151 A * 3/1998 King et al. .................... 435/6

FOREIGN PATENT DOCUMENTS

| WO | WO 95/01441 | * | 1/1995 |
| WO | WO/95/01441 | * | 1/1995 |
| WO | WO 02/074903 A2 | * | 9/2002 |

OTHER PUBLICATIONS

Mahairas et al., Journal of Bacteriology 1996, vol. 178; pp. 1274-1282.
Pym et al., Molecular Microbiology 2002, vol. 46, pp. 709-717.
Renshaw et al., Journal of Biological Chemistry 2002, vol. 277; pp. 21598-21603.
Pallen, Trends in Microbiology 2002, vol. 10; pp. 209-212.
Pym et al., Nature Medicine 2003, vol. 9; pp. 533-539.
Renshaw et al., Journal of Biomolecular NMR 2004, vol. 30; pp. 225-226.
Okkels et al., Journal of bacteriology 2004, vol. 186; pp. 2487-2491.
Okkels et al., Proteomics 2004, vol. 4; pp. 2954-2960.

* cited by examiner

*Primary Examiner* — Vanessa L Ford
*Assistant Examiner* — Nina Archie
(74) *Attorney, Agent, or Firm* — Finnegan, Henderson, Farabow, Garrett & Dunner LLP

(57) ABSTRACT

A genetically modified strain of *M. tuberculosis* or *Mycobacterium bovis* BCG is provided, wherein the genetically modified strain comprises at least one modified sequence comprising SEQ ID NO: 1, SEQ ID NO: 2, or both, having at least one mutation at T2, Q4, F8, A14, L28, L29, W43, G45, Y51, Q55, Q56, N66, M83, V90, M93, or F94 in SEQ ID NO:1; or at least one mutation at Q3, F7 A13, L27, W42, G44, Y50, Q54, N65, N67, M82, V89, M92, or F93 in SEQ ID NO:2, or a deletion at the terminal end of less than 20 amino acids. In a preferred embodiment, the mutation is at least one of T2H, Q4L, F8I, AI4R, L28A, L29S, W43R, G45T, Q55I, Q56A, N66I, N67A, M83I, V90R, M93T, or F94Q in SEQ ID NO:1, and Q3L, F7I, A13R, L27A, L28S, W42R, Q44T, Q54I, N65I, M82I, V89R, M92T, and F93Q in SEQ ID NO:2. Similarly, the genetically modified strain may also secrete ESAT-6 with a hexa-histidine tag, tetra-cysteine tag, or FLAG-tag, a GFP-fusion, or a short truncation at the C-terminal end of less than 20 amino acids.

10 Claims, 16 Drawing Sheets

MODIFIED ESAT-6 MOLECULES AND IMPROVED VACCINE STRAINS OF *MYCOBACTERIUM BOVIS* BCG

CROSS-REFERENCE TO RELATED APPLICATIONS

This application is based on and claims the benefit of U.S. Provisional Application No. 60/692,561, filed Jun. 22, 2005. The entire disclosure of this application is relied upon and incorporated by reference herein.

FIELD OF THE INVENTION

This invention relates to functional analysis of ESAT-6, the dominant T-cell antigen of *Mycobacterium tuberculosis*, and to its key residues involved in secretion, complex-formation, virulence and immunogenicity.

BACKGROUND OF THE INVENTION

Several attenuated or avirulent members of the *Mycobacterium tuberculosis* complex, like *Mycobacterium bovis* BCG (BCG), the vole *bacillus*. *Mycobacterium microti*, or the dassie *bacillus*, are deleted for an overlapping portion of the genome, known as region of difference 1 (RD1) (1-3). This segment is localized close to the origin of replication (4) in all fully virulent members of the complex (5) and harbors genes esxA, coding for the 6 kDa early secreted antigenic target (ESAT-6), and esxB, encoding the 10 kDa culture filtrate protein (CFP-10). The region was recently shown to be required for full virulence of *M. tuberculosis* (6-8), and when integrated into BCG, improved the ability of the recombinant BCG strain to protect against dissemination of tuberculosis in the mouse- and the guinea pig model (9).

Independent but complementary studies revealed that ESAT-6 and CFP-10 are secreted via the ESAT-6 system-1 (ESX-1), a dedicated secretion apparatus encoded by genes flanking esxA and esxB in the extended RD1 region (9-11). Among the proteins predicted to be involved in this process are a member of the AAA-family of ATPases (Rv3868), which may perform chaperone-like functions by assisting in the assembly and disassembly of protein complexes, and several putative membrane proteins with 1, 3 or 11 transmembrane domains (Rv3869, Rv3870, Rv3877), or ATP binding sites (Rv3871), which could be involved in forming a trans-membrane channel for the translocation of the effector molecules.

Although several publications have recently addressed the function of this secretion system (7, 9-14), there is a need in the art for information relating to the effector proteins.

SUMMARY OF THE INVENTION

This invention aids in fulfilling the needs in the art by providing a genetically modified strain of *Mycobacterium* of *Mycobacterium tuberculosis* complex and preferably *M. tuberculosis* or *Mycobacterium bovis* BCG, wherein the genetically modified strain produces at least one polypeptide comprising modified sequence SEQ ID NO: I, SEQ ID NO: 2, or both, having at least one mutation at T2, Q4, F8, A14, L28, L29, W43, G45, Y51, Q55, Q56, N66, M83, V90, M93, or F94 in SEQ ID NO:1, or a deletion at the C-terminal end of less than 20 amino acids; or at least one mutation at 03, F7, A13, L27, W42, G44, Y50, Q54, N65, N67, M82, V89, M92, or F93 in SEQ ID NO:2, or a deletion at the terminal end of less than 20 amino acids. In a preferred embodiment, the mutation is at least one of T2H, Q4L, F8I, A14R, L28A, L29S, W43R, G45T, Q55I, Q56A, N66I, N67A, M83I, V90R, M93T, or F94Q in SEQ ID NO:1, and Q3L, F7I, A13R, L27A, L28S, W42R, G44T, Q54I, N65I, M82I, V89R, M92T, and F93Q in SEQ ID NO:2, and the deletion is from amino acid 84 to amino acid 95. The genetically modified strain can further comprise a hexa-histidine tag, a tetra-cysteine tag, a FLAG-tag, or a GFP polypeptide.

SEQ ID NO: 1 is the amino acid sequence shown in FIG. 1A for *M. tuberculosis*.

SEQ ID NO: 2 is the amino acid sequence shown in FIG. 1A for *M. leprae*.

The locations of the mutations in SEQ ID NO: 1 and SEQ ID NO: 2 are shown by the numbered residues below the sequences in FIG. 1A. This invention concerns a genetically modified strain of *Mycobacterium* of *Mycobacterium tuberculosis* complex and preferably *M. tuberculosis* or *Mycobacterium bovis* BCG, wherein the genetically modified strain produces at least one modified polypeptide comprising SEQ ID NO: 1, SEQ ID NO: 2, or both, having a deletion of the extreme C-terminal end, outside the helical region of the polypeptide. Preferably the deleted amino acids are the last 12 C-terminal residues.

This invention provides a genetically modified strain of *Mycobacterium tuberculosis* complex, wherein the genetically modified strain produces a recombinant polypeptide comprising SEQ ID NO: 1, SEQ ID NO: 2 or esxB and a small tag. The small tag can be chosen from among hexa-histidine tag, tetra-cysteine tag, and FLAG tag.

A genetically modified strain of *Mycobacterium tuberculosis* complex is provided, wherein the genetically modified strain produces a recombinant polypeptide comprising SEQ ID NO: 1, SEQ ID NO: 2 or esxB and a small tag, and wherein the genetically modified strain induce an IFN-γ response to ESAT-6 and/or CFP-10 antigens.

A genetically modified strain of *Mycobacterium tuberculosis* complex is provided, wherein the genetically modified strain produces a recombinant polypeptide comprising SEQ ID NO: 1, SEQ ID NO: 2, or esxB fused to a reporter polypeptide, such as GFP.

This invention also provides deposits of biological material.

In addition, this invention provides a method of modulating an immune response in a host, wherein method comprises administering to the host a genetically modified strain of the invention in an amount sufficient to modulate in the host an immune response to infection by at least one pathogen selected from *M. tuberculosis* and *M. leprae*. In a preferred embodiment of the invention the immune response is a protective immune response against at least one of the pathogens.

Further, this invention provides a purified composition consisting essentially of early secreted antigenic target protein of about 6 kDa (ESAT-6) complexed with culture filtrate protein of about 10 kDa (CFP-10) of *Mycobacterium tuberculosis*. The purified complex can comprise a detectable tag, such as hexa-histidine.

A purified antibody that immunologically reacts with the complex of the invention is also provided. The antibody can be a polyclonal antibody or a monoclonal antibody.

An immunogenic composition of the invention comprises the genetically modified strain and a pharmaceutically acceptable carrier therefor. The composition can be a vaccine.

In addition, this invention provides a modified sequence comprising SEQ ID NO: I, SEQ ID NO: 2, or both, having at least one mutation at T2, Q4, F8, A14, L28, L29, W43, G45, Y51, Q55, Q56, N66, M83, V90, M93, or F94 in SEQ ID NO:1; or at least one mutation at Q3, F7, A13, L27, W42, G44, Y50, Q54, N65, N67, M82, V89, M92, or F93 in SEQ ID NO:2, or a deletion at the terminal end of less than 20 amino acids. In a preferred embodiment, the mutation is at least one of T2H, Q4L, F8I, AI4R, L28A, L29S, W43R, G45T, Q55I, Q56A, N66I, N67A, M83I, V90R, M93T, or F94Q in SEQ ID NO:1, and Q3L, F7I, A13R, L27A, L28S, W42R, G44T, Q54I, N65I, M82I, V89R, M92T, and F93Q in SEQ ID NO:2, or a deletion at the C-terminal end of less than 20 amino acids. Nucleic acid molecules encoding these modified sequences are also within the scope of this invention.

In addition, this invention provides a vector comprising a nucleic acid molecule of the invention and a host cell comprising the vector. In a preferred embodiment, the host cell is *Mycobacterium bovis* BCG.

In addition, this invention provides a vector coding for a polypeptide comprising SEQ ID NO: 1, SEQ ID NO: 2, or both or SEQ ID NO: 1, SEQ ID NO: 2 or both having mutations as described above, and further comprising a detectable tag, such as hexa-histidine (HHHHH) (SEQ ID NO: 71), Tetra cysteine-tag (FLNCCPGCCMEP) (SEQ ID NO: 72), or FLAG (DYKDDDDK) (SEQ ID NO: 73). A host cell containing the vector is also provided.

This invention further provides a method for screening a large range of chemical substances that may inhibit the ESX-1 secretion system, wherein the method comprises the steps of:
   a) contacting the chemical substance to screen with a culture of a genetically modified strain;
   b) detecting presence of ESAT-6 and/or CFP-10 in the supernatant of the culture by immunological tools (antibodies), and
   c) determining the inhibitor activity of the chemical substance on the ESX-1 secretion system when ESAT-6 and/or CFP-10 are not detected in the supernatant or detected in a lesser quantity than without the chemical substance.

A fluorescent antibody can be used for detecting ESAT-6 and/or CFP-10 in the supernatant of the culture.

A therapeutical method of the invention that relies on Th1 mediated immunity comprises administering a genetically modified strain of the invention or a composition of the invention.

The therapeutical method can be used to treat bladder cancer or asthma.

This invention provides method for screening mutations in SEQ ID NO: 1 or SEQ ID NO: 2 that inhibit the formation of complex ESAT-6-CFP-10, wherein the method comprises the following steps:
   a) mutagenesis of a genetically modified strain of the invention,
   b) culture of the mutagenized strain obtained at step a) and recovering the culture supernatant,
   c) affinity purification of the recombinant polypeptide comprising SEQ ID NO: 1, SEQ ID NO: 2 or esxB and a small tag,
   d) immunologically detecting the presence of ESAT-6 and CFP-10 in the affinity purification eluate of step c), and
   e) determining that the mutation is a mutation that inhibits the formation of the complex ESAT-6-CFP-10 if the two polypeptides ESAT-6 and CFP-10 are not both detected in the affinity purification eluate.

The genetically modified strain thus obtained by the method of is also provided.

This invention includes the use of at least one polypeptide of the invention as antigen in a diagnostic kit for detecting a *Mycobacterium* infection and discriminating between an infection caused by *Mycobacterium tuberculosis* and infections caused by environmental pathogenic mycobacterial strains secreting an ESAT-6 ortholog but not belonging to *M. tuberculosis* complex. The pathogenic mycobacterial strains to discriminate from *M. tuberculosis* can be *Mycobacterium kansasii*, *Mycobacterium smegmatis*, *Mycobacterium marinum*, and *Mycobacterium szulgai*.

BRIEF DESCRIPTION OF THE DRAWINGS

This invention will be described in greater detail with reference to the drawings in which:

Figure 8:
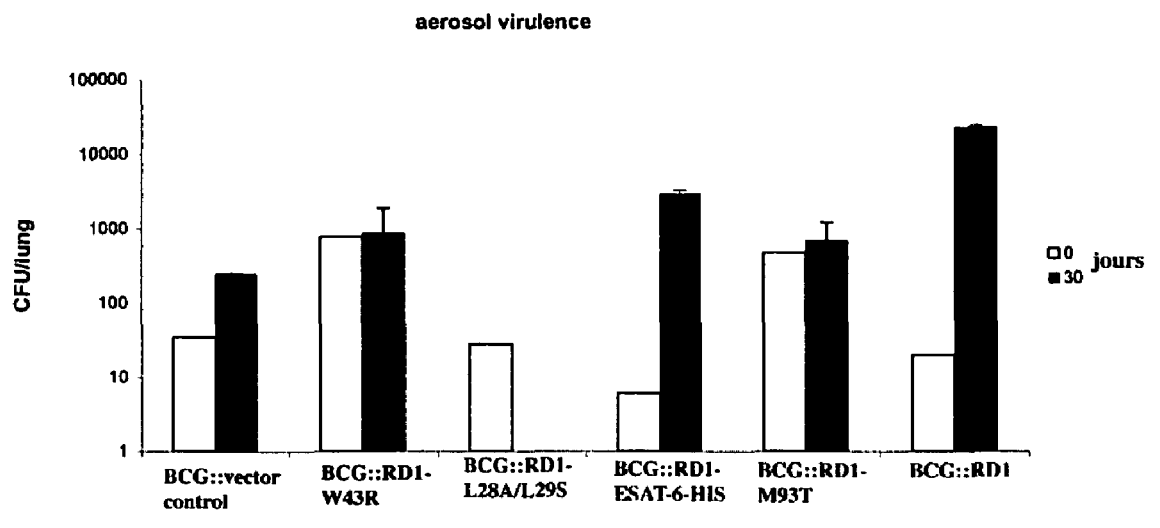

FIG. 8. The results of virulence testing of recombinant BCG strains are depicted. Specifically, C57BL/6 mice were subjected to aerosol infections with the recombinant strains. Bacterial loads 30 days post-infection are shown in the Figure.

FIG. 9(A) depicts CFU in the lungs in the first round of the protection study. FIG. 9(B) depicts CFU in the spleen in the first round of the protection study.

FIG. 10(A) depicts CFU in the lungs in the second round of the protection study. FIG. 10(B) depicts CFU in the spleen in the second round of the protection study.

DETAILED DESCRIPTION OF THE INVENTION

ESAT-6 and CFP-10, which have been shown to form a 1:1 complex in vitro (15), belong to a large family of small proteins identified in Gram positive bacteria. Proteins of this family have a size of around 100 amino acids and are characterized by a conserved motif Trp-X-Gly (WXG) (16). To further elucidate the structure—function relationship in members of the ESAT-6, or WXG, family, a strategy has been developed to study variants of ESAT-6 in its natural bacterial host. The residues to be modified were selected according to their potential importance for secretion, immunogenicity and virulence. Among them were several amino acids that are highly conserved among ESAT-6 orthologs from different bacterial species. Other regions of interest were the amino- and carboxy termini of the protein. It was also of interest to identify modifications that would allow specific binding of biologically active ESAT-6 to selected matrices, and modifications that may be used to localize ESAT-6 in cell biological experiments. This invention relates to the behavior of these mutant strains in immunogenicity and virulence tests relative to control strains and show how the modifications allowed new features of ESAT-6 and the corresponding secretion system to be discovered.

The combined efforts of this invention using bioinformatics, protein engineering, as well as immunological and virulence studies made it possible to pinpoint regions of the ESAT-6 molecule that are critical for its biological activity. The invention has clearly shown that it is indeed ESAT-6, in combination with CFP-10 that mediates ESX-1-associated virulence. This invention demonstrates that mutation of only one or two selected residues in ESAT-6 can abolish the virulent phenotype of the recombinant *M. tuberculosis* strain and links this phenomenon in part to the destruction of the α-helical/coiled-coil motifs present in ESAT-6 and its protein partner CFP-10.

Figure 6:
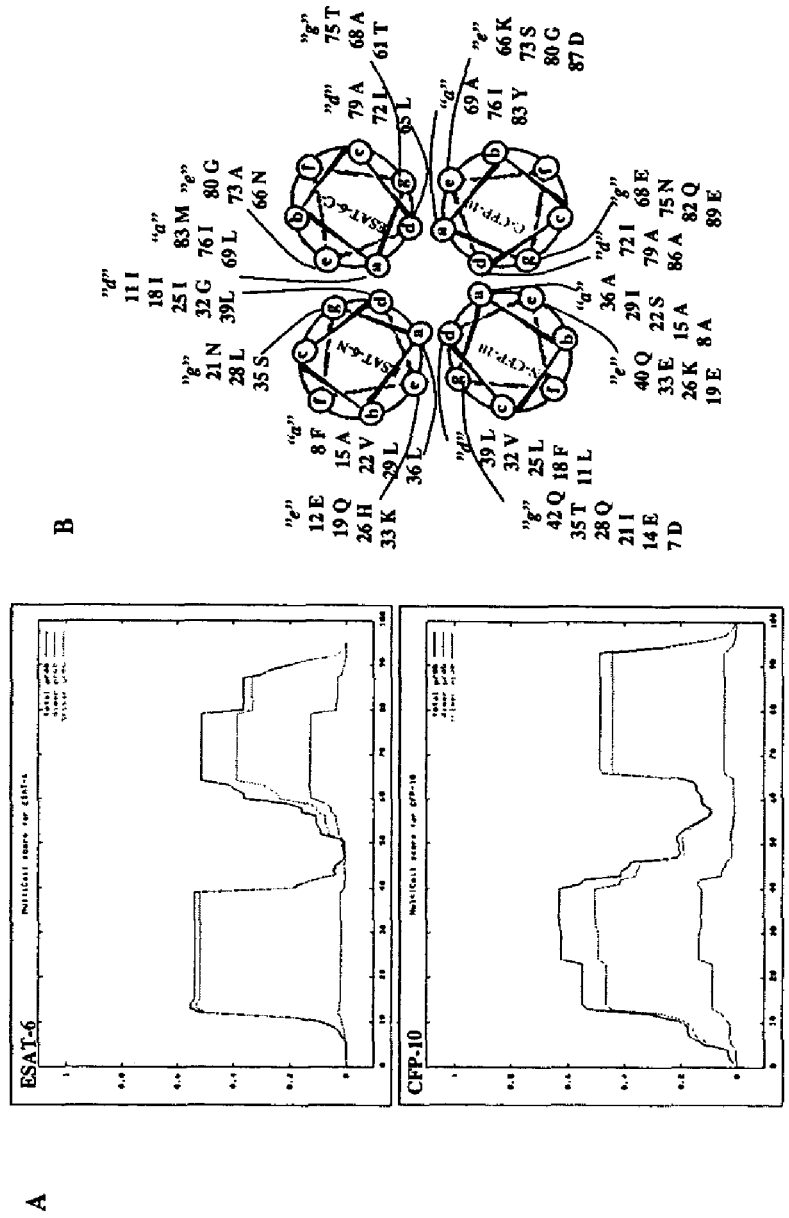
FIG. 6. A) Probability plots for the formation of the coiled-coil structures within ESAT-6 and CFP-10 obtained by the use of the Multicoil program. B) Putative organization of the ESAT-6 and CFP-10 helical strands, showing residues that potentially contribute to the characteristic abcdefg seven-residue repeat.

The sequences of coiled-coils in proteins consist of heptad repeats denoted "abcdefg", harboring two characteristic hydrophobic positions at sites "a" and "d" of an α-helix (23). Amino acids in other positions, in particular in "e" and "g", are often polar residues important for the water solubility of the protein complex and the specificity of interactions between neighboring helices at different pH levels (FIG. 6). It has been shown that short stretches of 30 to 40 residues may be sufficient to account for such interaction of proteins (24). It is interesting to note that many proteins involved in type III secretion systems of Gram-negative bacteria contain coiled-coil motifs, which enable or stabilize protein-protein interactions (25). In the case of ESAT-6 and CFP-10 the presence of multimeric, but not dimeric coiled-coil motifs (FIG. 6A), supposes that three or four helices may be involved in such an interaction. As described in the Examples section, the effects of the mutations introduced into ESAT-6 on virulence of recombinant strains can be rationalized from this model. The data confirm and extend predictions by Pallen, who described a large family of small proteins from Gram positive bacteria, including ESAT-6 and CFP-10 from *M. tuberculosis* or EsxA/B from *Staphylococcus aureus* (26), which are all characterized by the WXG motif and have a size of around 100 residues (16). The W43 residue could have a functional role in interacting with other proteins. However, in this model it is turned inward (on an "a" position) (FIG. 2) and helical in the published NMR results (19). It could, therefore, be important for structural reasons, interacting with another conserved hydrophobic amino acid, Y51 in ESAT-6.

Figure 3:
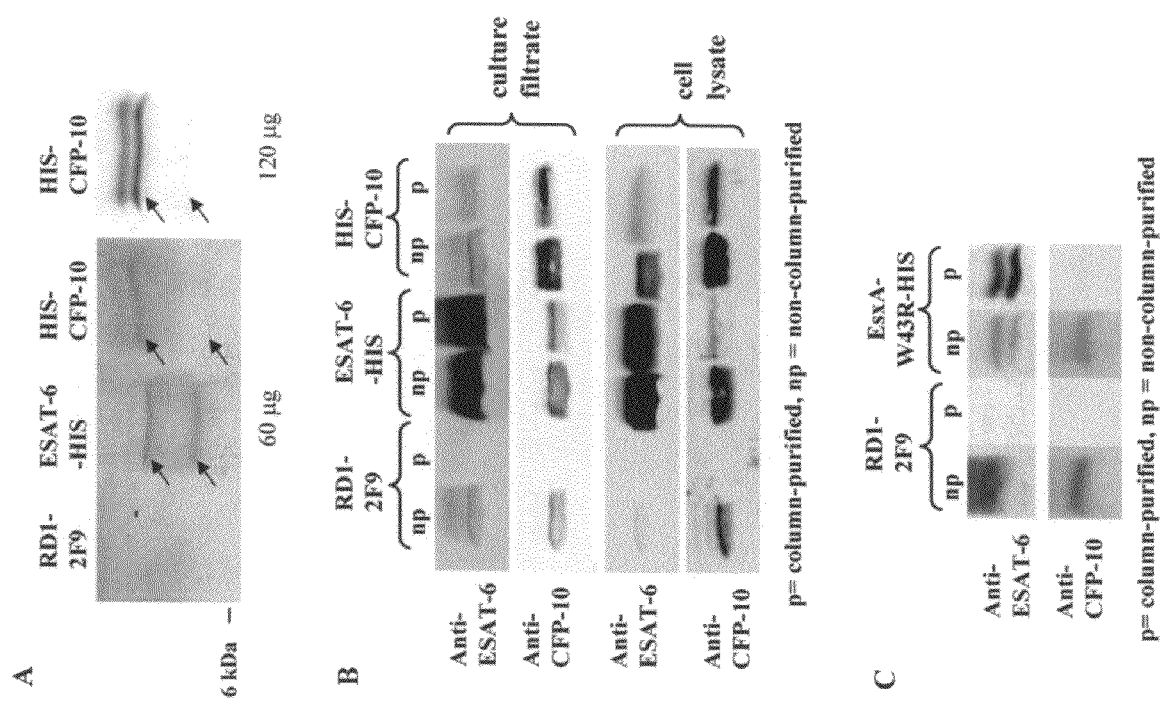
FIG. 3. Co-purification of ESAT-6 and CFP-10 from culture supernatants and cytosolic fractions of strains BCG::RD1-2F9, BCG::2F9-EsxA-HIS (ESAT-6-HIS) and BCG::2F9-HIS-EsxB (HIS-CFP-10) using Ni-NTA agarose mini columns A) Coomassie stained gel. Arrows indicate the presence of CFP-10 (EsxB) (upper) and ESAT-6-HIS (lower) bands. B) Western blotting analysis using either monoclonal anti-ESAT-6 antibodies or polyclonal anti-CFP-10 antibodies after purification of native (RD1-2F9) or hexahistidine-tagged proteins (ESAT-6-HIS, HIS-CFP-10) present in culture filtrate or cell lysate from recombinant BCG strains. C) Western blotting analysis using either monoclonal anti-ESAT-6 antibodies or polyclonal anti-CFP-10 antibodies after purification of native (RD1-2F9) or hexahistidine-tagged and W43R mutated ESAT-6 (EsxA-W43R-HIS) proteins present in culture filtrate of recombinant BCG.

Also, the almost perfect conservation of a tryptophan at this position in the whole protein family points to a structural role rather than a purely functional role. This hypothesis is supported by the observation that EsxA-W43R-HIS secreted by recombinant BCG did not retain CFP-10 by $Ni^{2+}$ affinity chromatography (FIG. 3C). The finding that replacement of a single residue severely disturbs binding to CFP-10 emphasizes the specificity of the ESAT-6/CFP-10 interaction, and may explain why ESAT-6 did not bind to other members of the Esx protein family (21, 22).

The neighboring mutation G45T seems to be important for the folding of ESAT-6, as glycine shows more flexibility and can adopt different conformations than other amino acids. It is, therefore, often found in short loops or turns.

Another attenuating mutation, L28A/L29S, can be explained by the prediction that L29 is at a "a" position, critical for the stability of the coiled-coil structure and also affecting secretion. Finally, two mutations showing attenuating effects, V90R, and F94Q are both in the extreme C-terminal end, outside the helical region. As the extreme C-terminus of ESAT-6 represents a floppy, structurally not well-defined region of the protein (19), it seems that mutation of residues at the C-terminus may inhibit a specific interaction of ESAT-6 with host proteins rather than affecting the structure or stability of the protein itself. It was recently shown that the C-terminus of ESAT-6 was apparently not involved in the protein interaction with CFP-10 (22), as is also suggested by this model. Moreover, based on this model, amino acids that are important for the correct function of CFP-10 can now be predicted and experimentally verified.

Research on ESAT-6 and the ESAT-6 system-1 has become an important topic for studies on the pathogenesis and immunogenicity of M. tuberculosis infections due to the outstanding role of ESAT-6 in these processes. However, to date many groups have used ESAT-6 molecules expressed by E. coli, and there are several examples in the literature that recombinant proteins may show characteristics that differ from the naturally occurring mycobacterial proteins (27). For this reason, one of the goals of this invention was to establish an experimental system in the M. tuberculosis complex that allows ESAT-6 to be studied while retaining the characteristics of the naturally occurring molecule.

Figure 7:
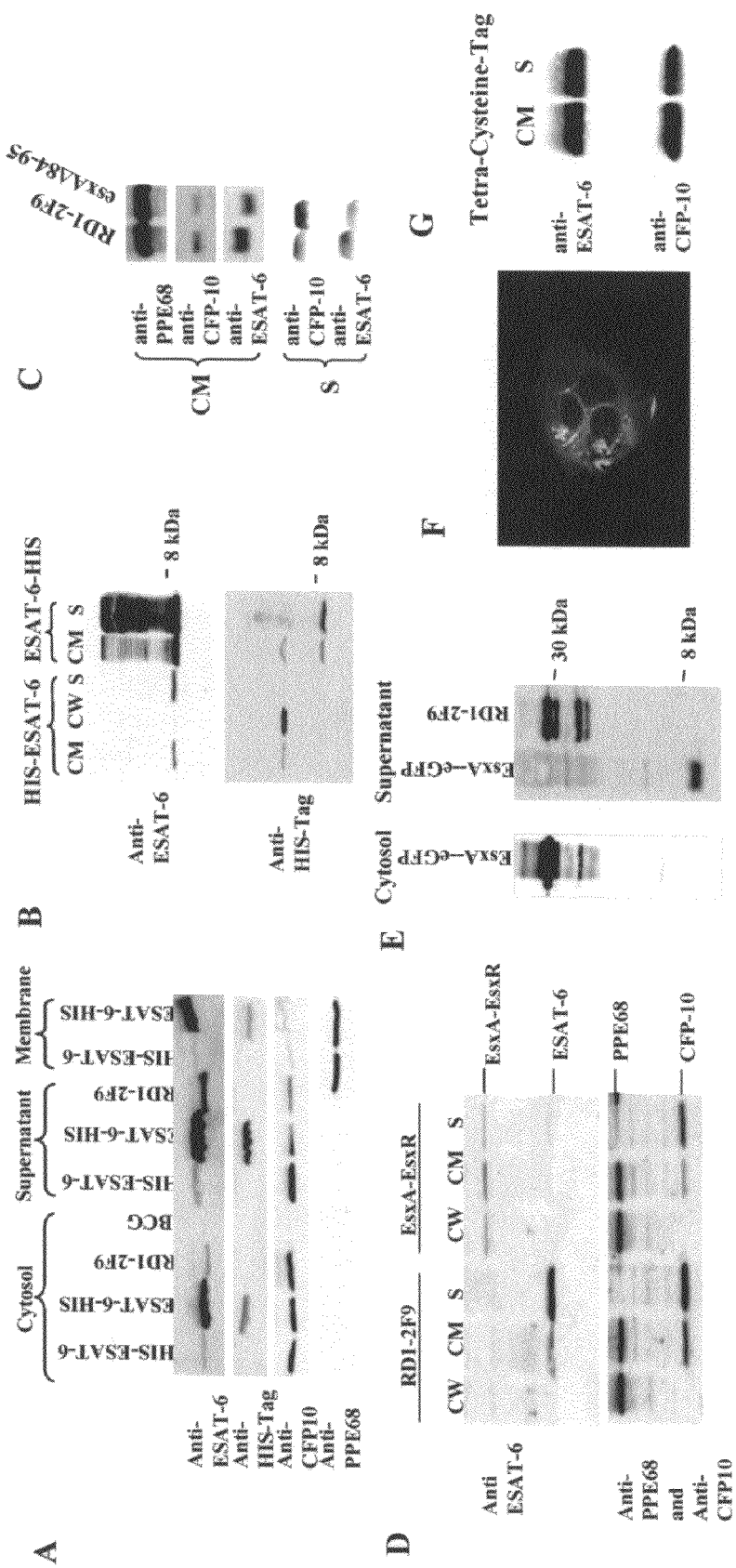
FIG. 7. (A) Immunoblot analysis of different cell fractions of BCG::2F9-HIS-EsxA (HIS-ESAT-6), BCG::2F9-EsxA-HIS (ESAT-6-HIS), BCG::RD1-2F9, and BCG, using a monoclonal anti-ESAT-6 antibody or polyclonal antibodies against Histidine tags, CFP-10 or PPE68. Note the size-difference between the native ESAT-6 and histidine tagged ESAT-6. (B) Immunoblot analysis of different cell fractions of BCG::2F9-HIS-EsxA (HIS-ESAT-6) and BCG::2F9-EsxA-HIS (ESAT-6-HIS) showing the cytosol-membrane (CM)-, the cell wall (CW)- and the supernatant (S)-fraction using an monoclonal ESAT-6 antibody or an anti-HIS tag antibody. Note that for construct BCG::2F9-HIS-EsxA an anti-HIS antibody binds to a large fragment that is retained in the cytosolic and membrane fraction, whereas the protein which reacts with the monoclonal ESAT-6 antibody has the usual size of ESAT-6 and does not react with the HIS-antibody, suggesting cleavage of the N-terminal HIS-tag. (C) Immunoblot analysis of different cell fractions of BCG::RD1-2F9 and BCG::RD1-2F9-esxAA84-95 using a monoclonal anti-ESAT-6 antibody or polyclonal antibodies against CFP-10 or PPE68. Note the size-difference between the native ESAT-6 and ESAT-6 deleted for the last 12 amino acids. (D) Immunoblot analysis of the cytosol-membrane (CM)-, the cell wall (CW)- and the supernatant (S)-fraction from strain BCG::2F9-EsxA-EsxR and BCG::RD1-2F9. (E) Immunoblot of the supernatant from BCG::2F9-EsxA-GFP and BCG::RD1-2F9 and using monoclonal anti-ESAT-6 antibodies. (F) Immunofluorescence microscope image of bone marrow derived murine macrophages that have ingested BCG::2F9-EsxA-GFP. (G) Immunoblot analysis of cytosol-membrane (CM)- and the supernatant (S)— fraction of BCG::RD1-2F9EsxA-Tetra-Cysteine-tag using a monoclonal anti-ESAT-6 antibody or polyclonal antibodies against CFP-10. Similar results were obtained for BCG::RD1-2F9EsxA-FLAG-tag (data not shown).
Figure 9A:
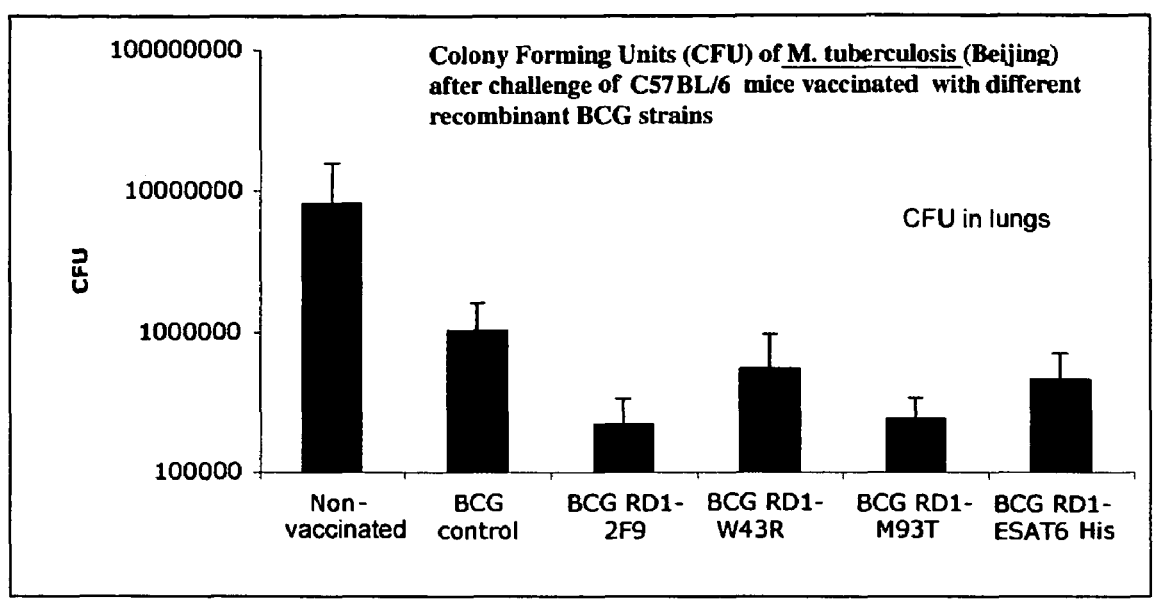
FIGS. 9(A) and 9(B). The results of a first round of a protection study of recombinant BCG strains are shown. Colony Forming Units (CFU) of *M. tuberculosis* (Beijing) after challenge of C57BL/6 mice vaccinated with different recombinant BCG strains are reported.
Figure 9B:
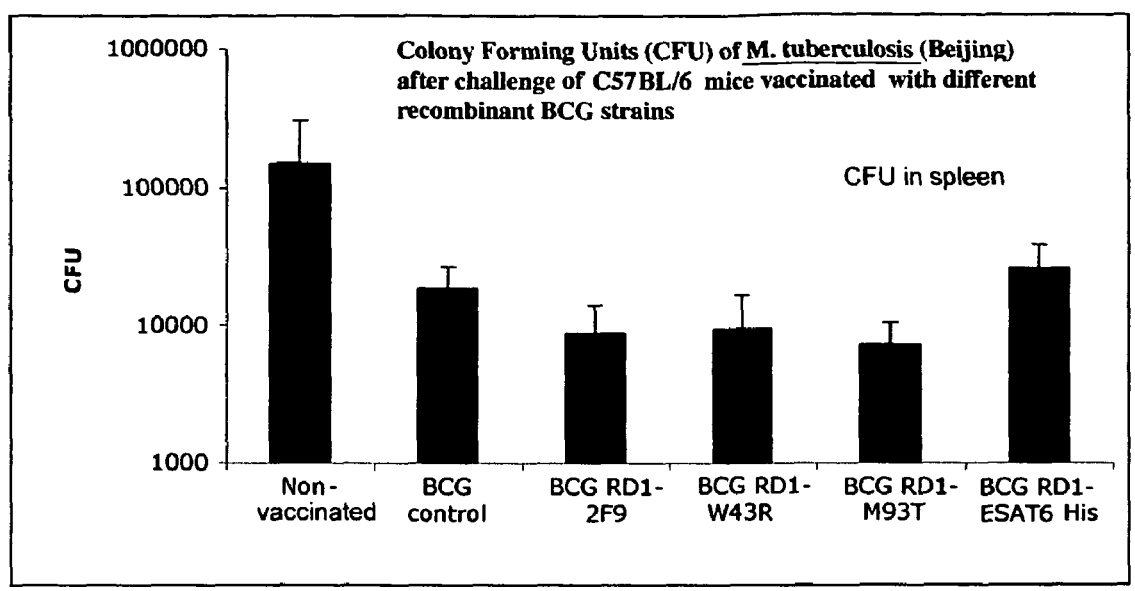
Figure 10A:
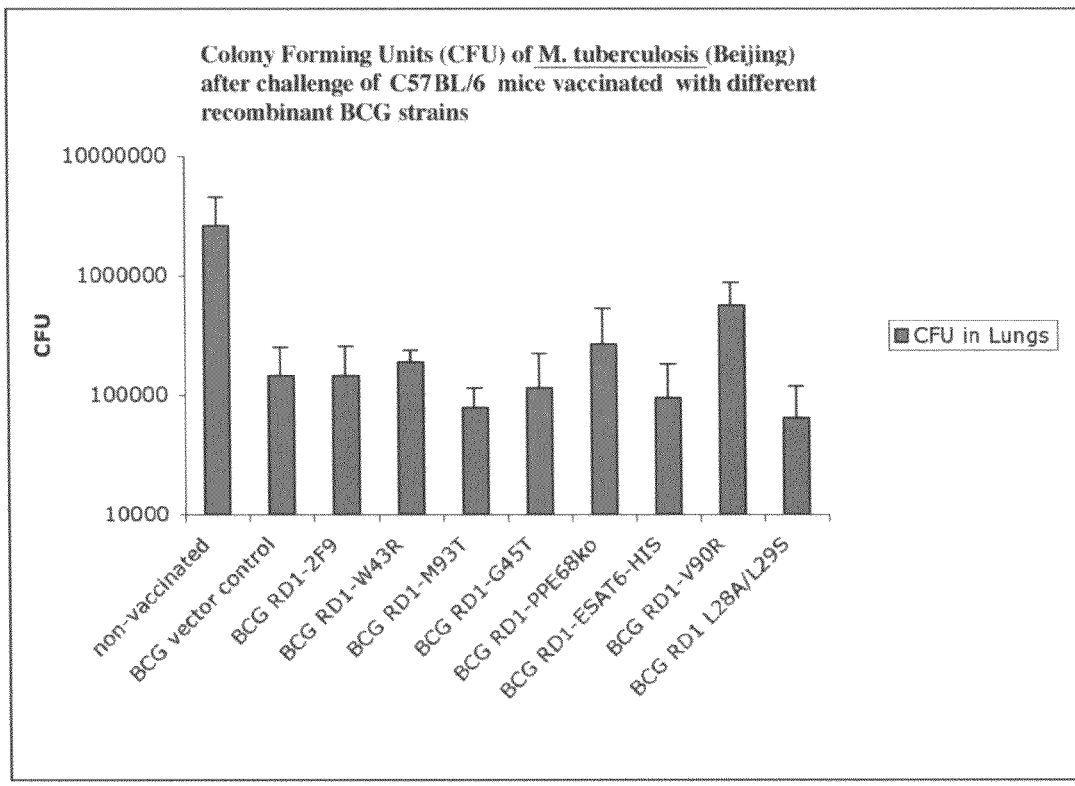
FIGS. 10(A) and 10(B). The results of a second round of a protection study of recombinant BCG strains are shown. Once again, colony forming units (CFU) of *M. tuberculosis* (Beijing) after challenge of C57BL/6 mice vaccinated with different recombinant BCG strains are reported.
Figure 10B:
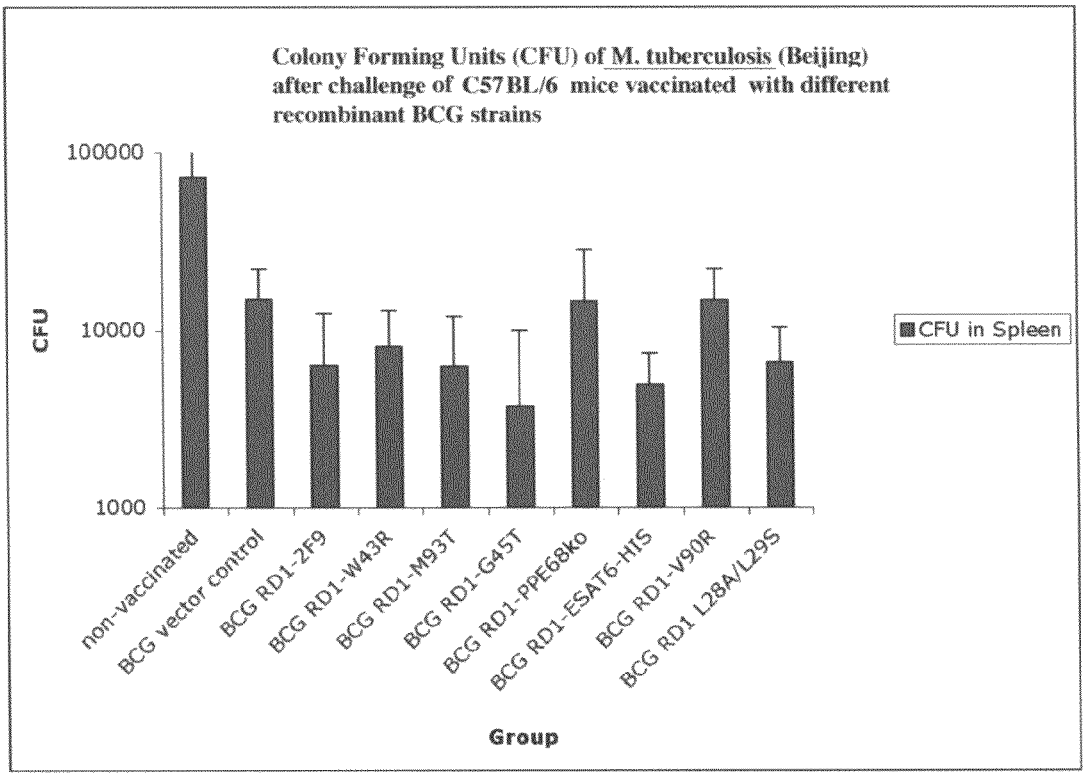
Figure 11A:
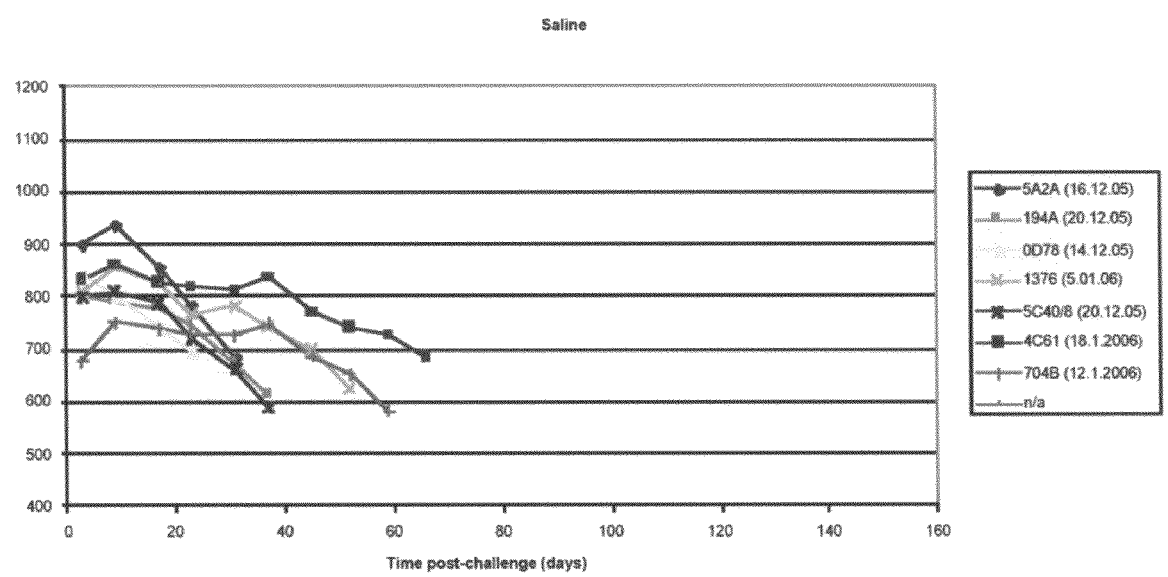
FIGS. 11(A), 11(B), and 11(C). The protective potential of recombinant strain BCG-RD1-ESAT-6-HIS (synonymous to BCG::2F9-EsxA-HIS) was evaluated in a guinea pig model. After vaccination with BCG or saline (non-vaccinated control) or BCG::RD1-2F9-EsxA-HIS (synonymous to BCG::RD1-ESAT-6-HIS), the animals were challenged with a *M. tuberculosis* H37Rv. Weight (in grams) was monitored as shown on the Y axis in FIGS. 11(A), 11(B), and 11(C)
Figure 11B:
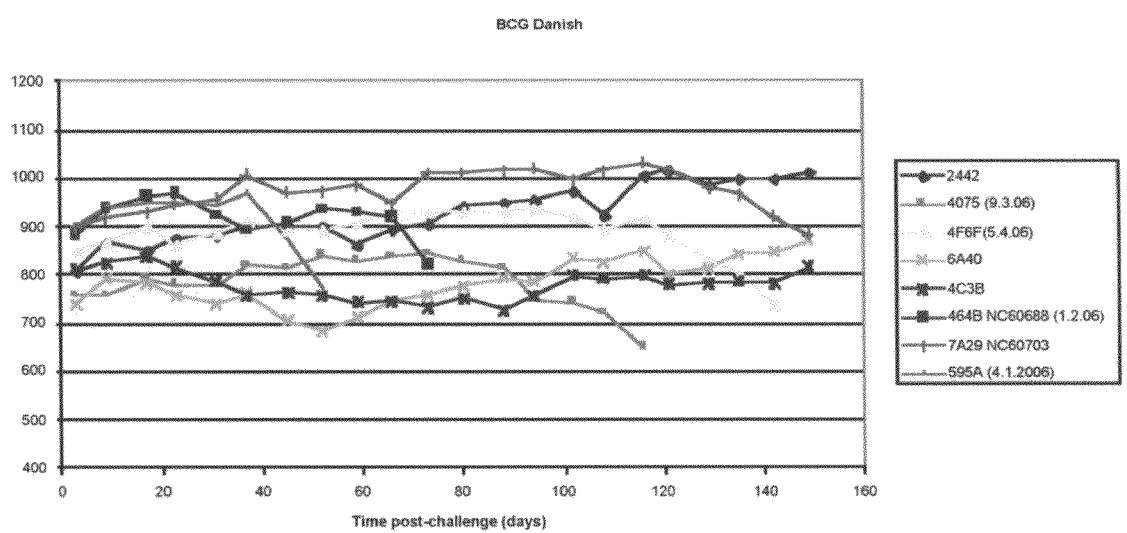
Figure 11C:
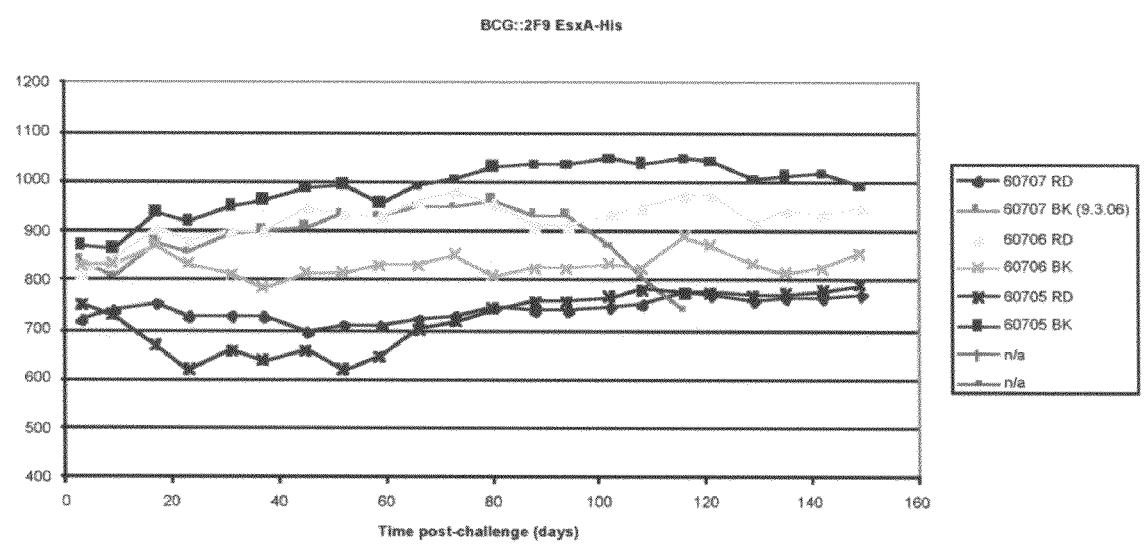
Figure 12:
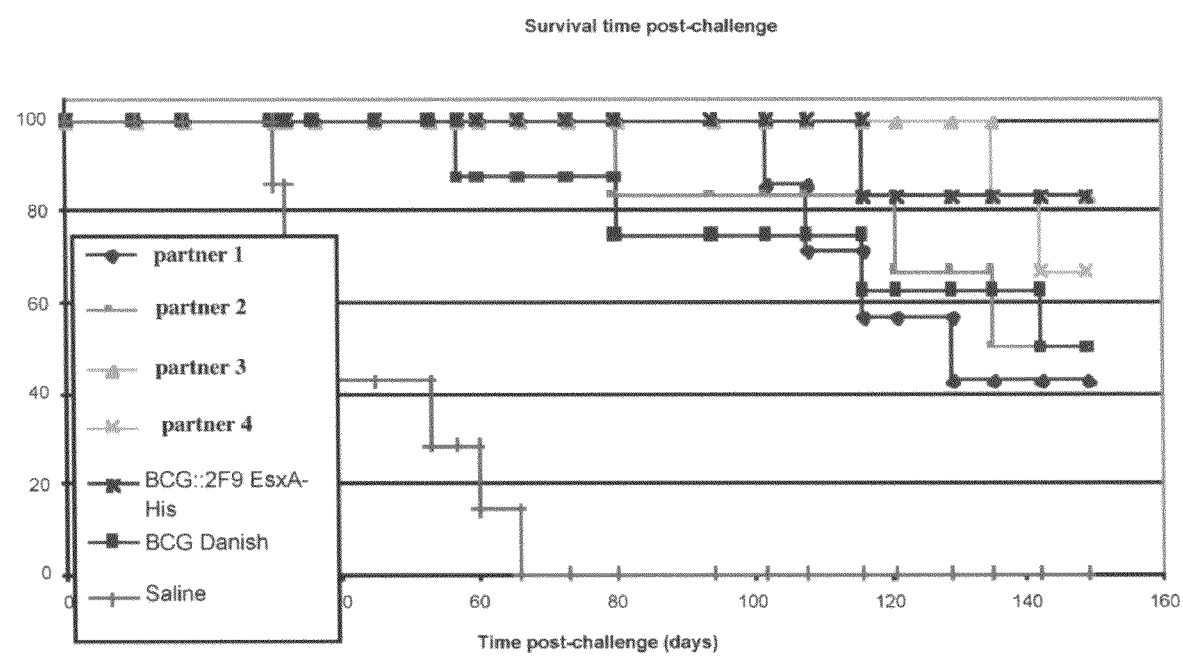
FIG. 12 is the overview of the guinea pig vaccination-challenge experiment.

In this respect, the C-terminal HIS construct of ESAT-6 was particularly interesting, as it fulfilled all these expected features. In contrast to predictions based on E. coli-expressed ESAT-6 (15), proteolytic cleavage of the 11 C-terminal residues did not occur for ESAT-6 expressed by BCG and M. tuberculosis. So far, in all ESAT-6 constructs that contained C-terminal tags or fusions there was observed a size shift, and no detection of molecules that had lost their tag (FIG. 7). The results obtained with co-purification assays, indicating that CFP-10 was eluted together with the HIS-tagged ESAT-6 protein from a $Ni^{2+}$ affinity column after passage of supernatant from recombinant BCG is the first proof that indeed, in a biologically relevant, non-denatured state, ESAT-6 and CFP-10 form a protein complex even after secretion. As the BCG::2F9-EsxA-HIS strain retained intermediate virulence and specific immunogenicity, short tags added at the C-terminus of the ESAT-6 protein do not seem to alter greatly the biological activity of ESAT-6 produced by recombinant BCG.

With this knowledge, it is now possible to create recombinant BCG strains secreting ESAT-6 with small C-terminal tags, like BCG::2F9-EsxA-Tetra-cysteine-tag (FIG. 7G) or BCG::2F9-EsxA-FLAG-tag, applicable to cell biological experiments that are needed to investigate targeting and trafficking of ESAT-6 in macrophages or dendritic cells.

Certain isoforms of the ESAT-6 molecule from M. tuberculosis, separated by 2-DE, were identified as carrying a post translational modification, namely, an acetylation of the threonine residue at position 2, and it was observed that only the unacetylated form of ESAT-6 interacted with CFP-10 (28). Acetylation affects diverse protein functions like enzyme activity, stability and protein-protein interactions (29), but the role of the acetylation of ESAT-6 during infection with M. tuberculosis is not known. This was one of the reasons why a mutant strain H37RvΔRD1::2F9EsxA-T2H, which had the threonine replaced by histidine, was constructed. However, as the mutant strain secreted ESAT-6 normally and retained the enhanced in vivo growth in SCID mice, it was concluded that this particular post-translational modification of the T2 residue in ESAT-6 does not have a major effect upon its function.

The observation that mutations in ESAT-6, which diminish or abolish virulence, also inhibit ESAT-6 specific T-cell responses in mice clearly demonstrates that optimal recognition of ESAT-6 by the immune system not only requires secretion of the antigen but also needs a biologically active form of ESAT-6. The finding that a mutation at the C-terminus oblates immunogenicity upon stimulation with the N-terminal ESAT-6 peptide 1-20 opens future studies on antigen processing and innate and/or adaptive immune responses. The immune recognition may depend on proper trafficking of ESAT-6, and this process possibly requires interaction of ESAT-6 with—as yet unknown—host proteins.

In a more practical perspective, the use of the ESAT-6-HIS constructs expressed by BCG opens up new ways to identify such proteins. Furthermore, ESAT-6-HIS, EsxA-Tetra-cysteine-tag, EsxA-FLAG-tag and/or ESAT-6-GFP constructs should enable high-throughput screening procedures to be established, to identify potential inhibitors of the ESAT-6 system-1, which in turn could lead to the identification of new anti-tuberculous drugs. As another application, certain strains secreting mutated or tagged ESAT-6 with intermediate virulence are promising candidates for new, more effective vaccines that combine lower virulence, than the previously tested BCG::RD1-2F9 strain (12), with the beneficial effects of strong T-cell responses against the immunodominant proteins ESAT-6 and CFP-10 (9).

Expression Systems

The present invention provides recombinant cloning and expression vectors containing DNA, as well as host cell containing the recombinant vectors. Expression vectors comprising DNA may be used to prepare the polypeptides or fragments of the invention encoded by the DNA. A method for producing polypeptides comprises culturing host cells transformed with a recombinant expression vector encoding the polypeptide, under conditions that promote expression of the polypeptide, then recovering the expressed polypeptides from the culture. The skilled artisan will recognize that the procedure for purifying the expressed polypeptides will vary according to such factors as the type of host cells employed, and whether the polypeptide is membrane-bound or a soluble form that is secreted from the host cell.

Any suitable expression system may be employed. The vectors include a DNA encoding a polypeptide or fragment of the invention, operably linked to suitable transcriptional or translational regulatory nucleotide sequences, such as those derived from a mammalian, microbial, viral, or insect gene.

Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the polypeptide. The signal peptide is cleaved from the polypeptide upon secretion of polypeptide from the cell.

Suitable host cells for expression of polypeptides include prokaryotes, yeast or higher eukaryotic cells. Mammalian or insect cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce polypeptides using RNAs derived from DNA constructs disclosed herein.

Prokaryotic Systems

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. The use of *Mycobacterium* host cells, such as *M. bovis* BCG, *M. tuberculosis, M. microti*, and *M. smegmatis*, is preferred. The use in *M. smegmatis* is particularly preferred. In a prokaryotic host cell, such as *E. coli*, a polypeptide may include an N-terminal methionine residue to facilitate expression of the recombinant polypeptide in the prokaryotic host cell. The N-terminal Met may be cleaved from the expressed recombinant polypeptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage 8P$_L$ promoter and a cI857ts thermolabile repressor sequence. Plasmid vectors available from the American Type Culture Collection which incorporate derivatives of the 8P$_L$ promoter include plasmid pHUB2 (resident in *E. coli* strain JMB9, ATCC 37092) and pPLc28 (resident in *E. coli* RR1, ATCC 53082).

DNA may be cloned in-frame into the multiple cloning site of an ordinary bacterial expression vector. Ideally the vector would contain an inducible promoter upstream of the cloning site, such that addition of an inducer leads to high-level production of the recombinant protein at a time of the investigator's choosing. For some proteins, expression levels may be boosted by incorporation of codons encoding a fusion partner (such as hexahistidine) between the promoter and the gene of interest. The resulting "expression plasmid" may be propagated in a variety of strains of *E. coli*.

For expression of the recombinant polypeptide, the bacterial cells are propagated in growth medium until reaching a pre-determined optical density. Expression of the recombinant polypeptide is then induced, e.g. by addition of IPTG (isopropyl-b-D-thiogalactopyranoside), which activates expression of polypeptides from plasmids containing a lac operator/promoter. After induction (typically for 1-4 hours), the cells are harvested by pelleting in a centrifuge, e.g. at 5,000×G for 20 minutes at 4° C.

For recovery of the expressed polypeptide, the pelleted cells may be resuspended in ten volumes of 50 mM Tris-HCl (pH 8)/1 M NaCl and then passed two or three times through a French press. Most highly expressed recombinant polypeptides form insoluble aggregates known as inclusion bodies. Inclusion bodies can be purified away from the soluble polypeptides by pelleting in a centrifuge at 5,000×G for 20 minutes, 4° C. The inclusion body pellet is washed with 50 mM Tris-HCl (pH 8)/1% Triton X-100 and then dissolved in 50 mM Tris-HCl (pH 8)/8 M urea/0.1 M DTTf. Any material that cannot be dissolved is removed by centrifugation (10,000×G for 20 minutes, 20° C.). The polypeptide of interest will, in most cases, be the most abundant polypeptide in the resulting clarified supernatant. This polypeptide may be "refolded" into the active conformation by dialysis against 50 mM Tris-HCl (pH 8)/5 mM CaCl$_2$/5 mM Zn(OAc)$_2$/1 mM GSSG/0.1 mM GSH. After refolding, purification can be carried out by a variety of chromatographic methods, such as ion exchange or gel filtration. In some protocols, initial purification may be carried out before refolding. As an example, hexahistidine-tagged fusion proteins may be partially purified on immobilized Nickel.

While the preceding purification and refolding procedure assumes that the polypeptide is best recovered from inclusion bodies, those skilled in the art of polypeptide purification will appreciate that many recombinant proteins are best purified out of the soluble fraction of cell lysates. In these cases, refolding is often not required, and purification by standard chromatographic methods can be carried out directly.

Yeast Systems

Alternatively, the polypeptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene.

Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the polypeptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine, and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or Insect Systems

Mammalian or insect host cell culture systems also may be employed to express recombinant polypeptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture*, 1990, pp. 15-69). Additional protocols using commercially available reagents, such as Lipofectamine lipid reagent (Gibco/BRL) or Lipofectamine-Plus lipid reagent, can be used to transfect cells (Feigner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual*, 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology*, 1990). Smaller or larger SV40 fragments can also be used, provided the approximately 250 bp sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology*, 1997, pp. 529-534 and PCT Application WO 97/25420) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allow dicistronic mRNAs to be translated efficiently (Oh and Samow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology*, 1990). Exemplary expression vectors that employ dicistronic mRNAs are pTR-DC/GFP described by Mosser et al., *Biotechniques* 22:150-161, 1997, and p2A51 described by Morris et al., *Animal Cell Technology*, 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

Additional useful expression vectors, pFLAG® and pDC311, can also be used. FLAG® technology is centered on the fusion of a low molecular weight (1 kD), hydrophilic, FLAG® marker peptide to the N-terminus of a recombinant protein expressed by pFLAG® expression vectors. pDC311 is another specialized vector used for expressing proteins in CHO cells. pDC311 is characterized by a bicistronic sequence containing the gene of interest and a dihydrofolate reductase (DHFR) gene with an internal ribosome binding site for DHFR translation, an expression augmenting sequence element (EASE), the human CMV promoter, a tripartite leader sequence, and a polyadenylation site.

Regarding signal peptides that may be employed, a heterologous signal peptide or leader sequence may be used, if desired. The choice of signal peptide or leader may depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846.

Purification

The invention also includes methods of isolating and purifying the polypeptides and fragments thereof. An isolated and purified polypeptide according to the invention can be produced by recombinant expression systems as described above or purified from naturally occurring cells. The polypeptide can be substantially purified, as indicated by a single protein band upon analysis by SDS-polyacrylamide gel electrophoresis (SDS-PAGE). One process for producing polypeptides comprises culturing a host cell transformed with an expression vector comprising a DNA sequence that encodes the polypeptide under conditions sufficient to promote expression of polypeptide. The polypeptide is then recovered from culture medium or cell extracts, depending upon the expression system employed.

In one preferred embodiment, the purification of recombinant polypeptides or fragments can be accomplished using fusions of polypeptides or fragments of the invention to another polypeptide to aid in the purification of polypeptides or fragments of the invention. Such fusion partners can include a poly-His or other antigenic identification peptides.

With respect to any type of host cell, as is known to the skilled artisan, procedures for purifying a recombinant polypeptide or fragment will vary according to such factors as the type of host cells employed and whether or not the recombinant polypeptide or fragment is secreted into the culture medium.

In general, the recombinant polypeptide or fragment can be isolated from the host cells if not secreted, or from the medium or supernatant if soluble and secreted, followed by one or more concentration, salting-out, ion exchange, hydrophobic interaction, affinity purification or size exclusion chromatography steps. As to specific ways to accomplish these steps, the culture medium first can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. In addition, a chromatofocusing step can be employed. Alternatively, a hydrophobic interaction chromatography step can be employed. Suitable matrices can be phenyl or octyl moieties bound to resins. In addition, affinity chromatography with a matrix which selectively binds the recombinant protein can be employed. Examples of such resins employed are lectin columns, dye columns, and metal-chelating columns. Finally, one or more reversed-phase high performance liquid chromatography (RP-HPLC) steps employing hydrophobic RP-HPLC media, (e.g., silica gel or polymer resin having pendant methyl, octyl, octyldecyl or other aliphatic groups) can be employed to further purify the polypeptides. Some or all of the foregoing purification steps, in various combinations, are well known and can be employed to provide an isolated and purified recombinant polypeptide.

Recombinant polypeptide produced in bacterial culture is usually isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express a secreted polypeptide in order to simplify purification. Secreted recombinant polypeptide from a yeast host cell fermentation can be purified by methods analogous to those disclosed by Urdal et al. (J. Chromatog. 296:171, 1984). Urdal et al. describe two sequential, reversed-phase HPLC steps for purification of recombinant human IL-2 on a preparative HPLC column.

It is also possible to utilize an affinity column comprising a polypeptide-binding protein of the invention, such as a monoclonal antibody generated against polypeptides of the invention, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the invention.

The desired degree of purity depends on the intended use of the protein. A relatively high degree of purity is desired when the polypeptide is to be administered in vivo, for example. In such a case, the polypeptides are purified such that no protein bands corresponding to other proteins are detectable upon analysis by SDS-polyacrylamide gel electrophoresis (SDS-PAGE). It will be recognized by one skilled in the pertinent field that multiple bands corresponding to the polypeptide may be visualized by SDS-PAGE, due to differential glycosylation, differential post-translational processing, and the like. Most preferably, the polypeptide of the invention is purified to substantial homogeneity, as indicated by a single protein band upon analysis by SDS-PAGE. The protein band may be visualized by silver staining, Coomassie blue staining, or (if the protein is radiolabeled) by autoradiography.

The polypeptide or nucleic acid molecule is preferably 50%, 75%, 80%, 85%, 90%, 95%, or 98% pure, most preferably more than 99% pure.

Antibodies

Antibodies that are immunoreactive with the polypeptides and complexes of the invention are provided herein. Such antibodies specifically bind to the polypeptides and complexes via the antigen-binding sites of the antibody (as opposed to non-specific binding). Thus, the complexes and polypeptides, fragments, variants, fusion proteins, etc., as set forth above may be employed as immunogens in producing antibodies immunoreactive therewith. More specifically, the polypeptides, fragment, variants, fusion proteins, etc. contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, *Immuno Biology* 3:9 (Garland Publishing Inc., 2nd ed. 1996)). Because folded proteins have complex surfaces, the number of epitopes available is quite numerous; however, due to the conformation of the protein and steric hinderances, the number of antibodies that actually bind to the epitopes is less than the number of available epitopes (C. A. Janeway, Jr. and P. Travers, *Immuno Biology* 2:14 (Garland Publishing Inc., 2nd ed. 1996)). Epitopes may be identified by any of the methods known in the art.

Thus, one aspect of the present invention relates to the antigenic epitopes of the polypeptides and complexes of the invention. Such epitopes are useful for raising antibodies, in particular monoclonal antibodies, as described in detail below. Additionally, epitopes from the polypeptides and complexes of the invention can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides and complexes of the invention, whether the epitopes have been isolated or remain part of the polypeptides and complexes, both polyclonal and monoclonal antibodies may be prepared by conventional techniques as described below.

In this aspect of the invention, polypeptides and complexes can be utilized to prepare antibodies that specifically bind to polypeptides. The term "antibodies" is meant to include polyclonal antibodies, monoclonal antibodies, fragments thereof, such as F(ab')2 and Fab fragments, as well as any recombinantly produced binding partners. Antibodies are defined to be specifically binding if they bind polypeptides with a $K_a$ of greater than or equal to about $10^7$ $M^{-1}$. Affinities of binding partners or antibodies can be readily determined using conventional techniques, for example those described by Scatchard et al., *Ann. N.Y Acad. Sci.*, 51:660 (1949).

Polyclonal antibodies can be readily generated from a variety of sources, for example, horses, cows, goats, sheep, dogs, chickens, rabbits, mice, or rats, using procedures that are well known in the art. In general, a purified polypeptide or a peptide based on the amino acid sequence of polypeptide that is appropriately conjugated is administered to the host animal typically through parenteral injection. The immunogenicity of polypeptides and complexes can be enhanced through the use of an adjuvant, for example, Freund's complete or incomplete adjuvant. Following booster immunizations, small samples of serum are collected and tested for reactivity to polypeptides and complexes. Examples of various assays useful for such determination include those described in *Antibodies: A Laboratory Manual*, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. See, for example, the procedures described in U.S. Pat. Nos. RE 32,011, 4,902,614, 4,543,439, and 4,411,993; Monoclonal Antibodies, Hybridomas: *A New Dimension in Biological Analyses*, Plenum Press, Kennett, McKeam, and Bechtol (eds.), 1980. Briefly, the host animals, such as mice, are injected intraperitoneally at least once and preferably at least twice at about 3 week intervals with isolated and purified polypeptides or conjugated polypeptides, optionally in the presence of adjuvant. Mouse sera are then assayed by conventional dot blot technique or antibody capture (ABC) to determine which animal is best to fuse. Approximately two to three weeks later, the mice are given an intravenous boost of polypeptides or conjugated polypeptides. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as $^{125}$I-labeled polypeptide, is added to each well followed by incubation. Positive wells can be subsequently detected by autoradiography. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", *Strategies in Molecular Biology* 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., *Biotechnology*, 7:394 (1989).

Antigen-binding fragments of such antibodies, which may be produced by conventional techniques, are also encompassed by the present invention. Examples of such fragments include, but are not limited to, Fab and F(ab')$_2$ fragments. Antibody fragments and derivatives produced by genetic engineering techniques are also provided.

The monoclonal antibodies of the present invention include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al. (*Nature* 332: 323, 1988), Liu et al. (*PNAS* 84:3439, 1987), Larrick et al. (*Bio/Technology* 7:934, 1989), and Winter and Harris (*TIPS* 14:139, May, 1993). Procedures to generate antibodies transgenically can be found in GB 2,272,440, U.S. Pat. Nos. 5,569,825 and 5,545,806 and related patents claiming priority therefrom, all of which are incorporated by reference herein.

The invention provides immunogenic compositions, and more particularly, protective compositions for use in vaccines. The compositions can comprise the modified polypeptides of the invention. These compositions can also be employed as immunotherapy or vaccination drug therapy by administering the compositions to an animal, preferably a mammal. Effective quantities of the compositions of the invention can be administered to the mammal. The mammal that is treated by the method of the invention can be, but is not limited to, a dog, cat, cow, sheep, pig, goat, horse, monkey, or preferably, a human.

The mutant strains of the invention can be formulated as a pharmaceutical composition and administered in a variety of dosage forms adapted to the chosen route of administration, including, but not limited to, orally or parenterally, by intravenous, intramuscular, topical, or subcutaneous routes. Administration via the respiratory tract, such as by inhalation, can also be employed.

Thus, the mutant strains can be systemically administered, e.g., orally, in combination with a pharmaceutically acceptable vehicle, such as an inert diluent or an assimilable edible carrier. It can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations can be varied and may conveniently be between about 2 to about 60% of the weight of a given unit dosage form. The amount of active agent in such therapeutically useful compositions is such that an effective dosage level will be obtained.

The tablets, troches, pills, capsules, and the like can also contain the following: binders, such as gum tragacanth, acacia, corn starch or gelatin; excipients, such as dicalcium phosphate; a disintegrating agent, such as corn starch, potato starch, alginic acid and the like; a lubricant, such as magnesium stearate; and a sweetening agent, such as sucrose, fructose, lactose or aspartame or a flavoring agent, such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac or sugar and the like. A syrup or elixir can contain the active compound, sucrose or fructose as a sweetening agent, methyl and propylparabens as preservatives, a dye and flavouring, such as cherry or orange flavor. Of course, any material used in preparing any unit dosage form should be pharmaceutically acceptable and substantially non-toxic in the amounts employed. In addition, the active compound can be incorporated into sustained-release preparations and devices.

The active compound can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active agent in the required amount in the appropriate solvent with various of the other ingredients enumerated above, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

The ability of the compositions and vaccines of the invention to induce protective humoral immunity in a host can be enhanced by emulsification with an adjuvant, incorporating in a liposome, coupling to a suitable carrier, or by combinations of these techniques. In a preferred embodiment, the compositions of the invention can be administered with a conventional adjuvant, such as aluminum phosphate and aluminum hydroxide gel, in an amount sufficient to potentiate humoral or cell-mediated immune response in the host. Similarly, the compositions can be bound to lipid membranes or incorporated in lipid membranes to form liposomes. The use of nonpyrogenic lipids free of nucleic acids and other extraneous matter can be employed for this purpose.

The compositions and vaccines of the invention can be administered to the host in an amount sufficient to prevent or inhibit infection. In any event, the amount administered should be at least sufficient to protect the host, even though infection may not be entirely prevented.

An immunogenic response can be obtained by administering the compositions containing the modified polypeptides of the invention to the host in an amount of about 200 micrograms to about 1 mg, preferably about 500 micrograms per dose, by intramuscular injection in a subject. The dose depends upon whether the recipient is an infant, a child, an adolescent, or an adult, and also upon the health of the recipient. The composition of the invention can be administered together with a physiologically acceptable carrier. For example, a diluent, such as water or a saline solution, can be employed.

The immunization schedule will depend upon several factors, such as the susceptibility of the host to infection and the age of the host. A single dose of the composition of the invention can be administered to the host or a primary course of immunization can be followed in which several doses at intervals of time are administered. Subsequent doses used as boosters can be administered as needed following the primary course.

Another aspect of the invention provides a method of DNA vaccination. The method includes administering the expression vectors encoding at least one of the modified polypeptides of the invention, per se, with or without carrier molecules, to the subject.

Thus, the methods of treating include administering immunogenic compositions comprising the modified polypeptides, or compositions comprising nucleic acids encoding the modified polypeptides as well. Those of skill in the art are cognizant of the concept, application, and effectiveness of nucleic acid vaccines (e.g., DNA vaccines) and nucleic acid vaccine technology, as well as protein and polypeptide based technologies. The nucleic acid based technology allows the administration of nucleic acids encoding the modified polypeptides, naked or encapsulated, directly to tissues and cells without the need for production of encoded proteins prior to administration. The technology is based on the ability of these nucleic acids to be taken up by cells of the recipient cell or organism and expressed to produce an immunogenic determinant to which the recipient's immune system responds. Typically, the expressed antigens are displayed on the surface of cells that have taken up and expressed the nucleic acids, but expression and export of the encoded antigens into the circulatory system of the recipient individual is also within the scope of the present invention. Such nucleic acid vaccine technology includes, but is not limited to, delivery of expression vectors encoding the modified polypeptides. Although the technology is termed "vaccine", it is equally applicable to immunogenic compositions that do not result in a protective response. Such non-protection inducing compositions and methods are encompassed within the present invention. Although it is within the present invention to deliver nucleic acids encoding the modified polypeptides and carrier molecules, the present invention also encompasses delivery of nucleic acids as part of larger or more complex compositions.

In yet another embodiment, the invention provides a method of screening for compounds that modulate the ESAT-6 secretion system 1. Chemical compounds can be tested for their activity to block the ESAT-6 secretion machine, by monitoring fluorescence intensity of the supernatant of a culture from mycobacterial strains that have integrated modified versions of the RD1-2F9 cosmid, secreting tagged ESAT-6 molecules (e.g. ESAT-6-GFP, EsxA-tetra-cysteine tag, or EsxA-FLAG-tag, or ESAT-HIS using appropriate antibodies). Throughout this application, various publications are referenced in parentheses by number. Full citations for these references may be found at the end of the specification immediately preceding the sequence listings and the claims. The disclosure of these publications in their entireties are hereby incorporated by reference into this application to describe more fully the art to which this invention pertains.

The following strains were deposited at the Collection Nationale de Cultures de Microorganismes (C.N.C.M.), of Institut Pasteur, 28, rue du Docteur Roux, F-75724 Paris, Cedex 15, France, and assigned the following Accession Nos.:

I-3461: mutation L28A/L29S in ESAT-6 gene

I-3463: mutation W43R in ESAT-6 gene

I-3460: mutation G45T in ESAT-6 gene

I-3462: mutation V90R in ESAT-6 gene

I-3459: mutation F94Q in ESAT-6 gene

I-3458: deletion 84-95 in ESAT-6 gene

I-3456: fusion ESAT-6 gene-HIS tag

I-3457: region RD1-2F9 deleted from ca. 4337 kb to ca. 4342 kb (2F9-delta rv3860-3866)

I-3464: 2F9EsxA-mod=library of various mutations in ESAT-6 gene (T2H, Q4L, F8I, A14R, Q55I/Q56A, N66I/N67A, M83I, M93T) and various gene fusions His tag-CFP10, ESAT-6-GFP, ESAT-6-tetra C tag and ESAT-6-FLAG tag.

I-3624: an *E. coli* strain containing the cosmid RD1-2F9EsxA-M93T

I-3625: an *E. coli* strain containing the cosmid RD1-2F9-delta rv 3860-3866.

Biological sample 2F9EsxA-delta 84-95 is *Escherichia coli* DH10B containing the cosmid 2F9EsxA-delta 84-95. Mutations were introduced in the ESAT-6 sequence of *Mycobacterium tuberculosis* in the cosmid RD1-2F9. Nucleotide modifications are shown in boldface in SEQ ID NO: 3.

Biological sample 2F9EsxA-mod is a plasmid library (cosmid 2F9) with clones that have modifications in the EsxA (ESAT-6). The clones are easy to differentiate either by sequencing or by stringent hybridization. Mutations were introduced in the ESAT-6 sequence of *Mycobacterium tuberculosis* in the cosmid RD1-2F9. Nucleotide modifications are shown in boldface in SEQ ID NOS: 4-15.

Biological sample 2F9-delta rv 3860-3866 is *Escherichia coli* DH10B containing the cosmid 2F9-delta rv 3860-3866. It contains only the region from *M. tuberculosis* H37RV starting from position ca. 4342, 200 and higher. Insert of cosmid 2F9-Delta-Rv3860-3866 (size 26379 bp) corresponding to sequence in the genome of *M. tuberculosis* H37Rv from 4342239 bp to 4368616 bp is shown in SEQ ID NO: 65.

Biological sample 2F9-ESAT-6-His is *Escherichia coli* DH10B containing the cosmid 2F9-ESAT-6-His. Mutations were introduced in the ESAT-6 sequence of *Mycobacterium tuberculosis* in the cosmid RD1-2F9. Nucleotide modifications are shown in boldface in SEQ ID NO: 16.

Biological sample 2F9EsxA-F94Q is *Escherichia coli* DH10B contained in cosmid 2F9EsxA-F94Q. To form 2F9EsxA-F94Q, mutations were introduced in the ESAT-6 sequence of *Mycobacterium tuberculosis* in the cosmid RD1-2F9. Nucleotide modifications are shown in boldface in SEQ ID NO: 20.

Biological sample 2F9 EsxA-G4ST is *Escherichia coli* DH10B containing the cosmid 2F9 EsxA-G4ST. Mutations were introduced in the ESAT-6 sequence of *Mycobacterium tuberculosis* in the cosmid RD1-2F9. Nucleotide modifications are shown in boldface in SEQ ID NO: 17.

Biological sample 2F9 EsxA-W43R is *Escherichia coli* DH10B containing the cosmid 2F9 EsxA-W43R. Mutations were introduced in the ESAT-6 sequence of *Mycobacterium tuberculosis* in the cosmid RD1-2F9. Nucleotide modifications are shown in boldface in SEQ ID NO: 18.

Biological sample 2F9EsxA-L28A/L295 is *Escherichia coli* DH10B containing the cosmid 2F9-EsxA-L28A/L295. Mutations were introduced in the ESAT-6 sequence of *Mycobacterium tuberculosis* in the cosmid RD1-2F9. Nucleotide modifications are shown in boldface in SEQ ID NO: 19.

Biological sample 2F9EsxA-V90R is *Escherichia coli* DH10B containing the cosmid 2F9-EsxA-V90R. Mutations were introduced in the ESAT-6 sequence of *Mycobacterium tuberculosis* in the cosmid RD1-2F9. Nucleotide modifications are shown in boldface in SEQ ID NO: 66.

This invention will be described in greater detail in the following Examples.

Example 1

Methods

Figure 5:
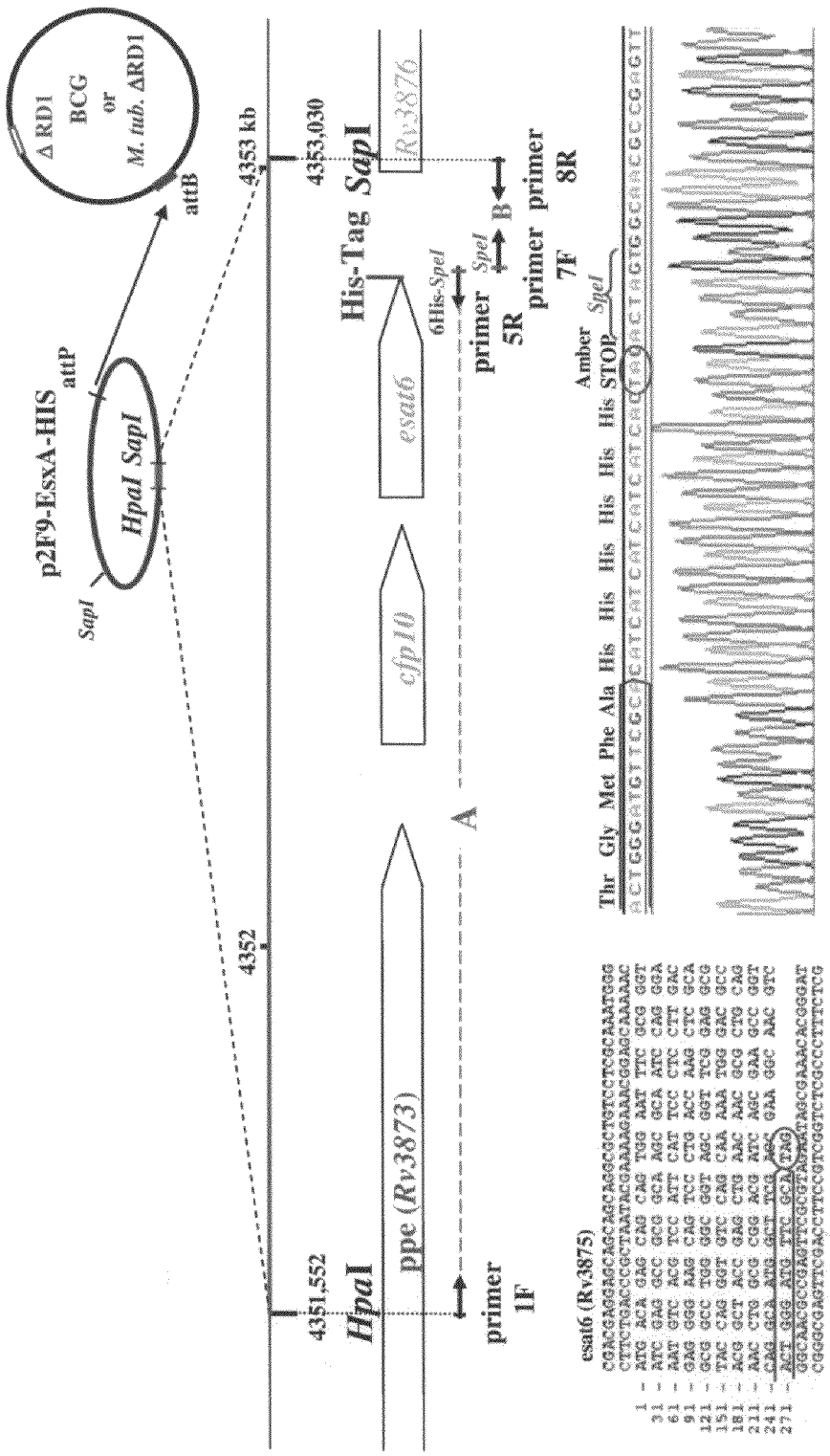
FIG. 5. Schematic representation of the strategy, which was used to obtain recombinant BCG and *M. tuberculosis* strains that express and secret genetically modified ESAT-6, for example, ESAT-6 with a C-terminal histidine tag (BCG::EsxA-HIS). Figure discloses SEQ ID NO: 67 and SEQ ID NO: 68 coding SEQ ID NO: 69, respectively, in order of appearance. 6×His tag disclosed as SEQ ID NO: 70.

A. Genetic Constructs and Mycobacterial Strains. An aim of the present invention was to introduce extra sequences or base substitutions into previously used cosmid pRD1-2F9 (12) to obtain BCG and/or *M. tuberculosis* strains that produce and secrete genetically modified variants of ESAT-6. The exact procedure is shown in FIG. 5 and is described above. The following primer sequences were used to introduce the various genetic modifications into pRD1-2F9.

| Primer | Sequence | SEQ ID NO |
|---|---|---|
| 1F: | GGAATTCCGTTAACACGCTTTTCGAGAG | SEQ ID NO: 21 |
| 2R: | CGGGATCCACTAGTCATGTTTTTGCTCCGTTTC | SEQ ID NO: 22 |
| 3F: | GCTCTAGACTAGTCATCATCATCATCATCACGAGCAGCAGTGGAATTTCGC | SEQ ID NO: 23 |
| 5R: | CGGGATCCACTAGTCTAGTGATGATGATGATGATGTGCGAACATCCCAGTGACG | SEQ ID NO: 24 |
| 7F: | GCTCTAGACTAGTGGCAACGCCGAGTTCGCG | SEQ ID NO: 25 |
| 8R: | CCCAAGCTTGGCCGGAAGAGCTTGTCG | SEQ ID NO: 26 |
| 12R: | CGGGATCCACTAGTCTACTTTCTCTCTTTACC | SEQ ID NO: 27 |
| 14F: | GCTCTAGACTAGTATGCATCATCATCATCATCACGCAGAGATGAAGACCGATGCCG | SEQ ID NO: 28 |
| 16R: | CGGGATCCACTAGTTGCGAACATCCCAGTGACG | SEQ ID NO: 29 |
| 17F: | GCTCTAGACTAGTTAGGGCAACGCCGAGTTCGCG | SEQ ID NO: 30 |
| 18F: | GCTCTAGACTATGGTTCGGAGGCGTACC | SEQ ID NO: 31 |
| 19R: | CGGGATCCACTAGTGCCCCAGGCCGCTGCG | SEQ ID NO: 32 |
| 22F: | GCTCTAGAGGCGCCGGTATCGAGGCCGCGGC | SEQ ID NO: 33 |
| 23R: | CGGGATCCCGATCGATATTCCACTGCTGCTCTGT | SEQ ID NO: 34 |
| 24F: | GCTCTAGAATGCATGAGCAGCAGTGGAATTTCG | SEQ ID NO: 35 |
| 25R: | CGGGATCCCGATGCATGTTTTTGCTCCGTTTCTT | SEQ ID NO: 36 |
| 27F: | GCTCTAGAGGCGCCAAATGGGACGCCACGGGTAC | SEQ ID NO: 37 |
| 28R: | CGGGATCCATCGATGACACCCTGGTACGCCTC | SEQ ID NO: 38 |
| 29R: | CGGGATCCATCGATCAGCTCGGTAGCCGTGGCG | SEQ ID NO: 39 |
| 30F: | GCTCTAGAGCGCCGCGCTGCAGAACCTGGC | SEQ ID NO: 40 |
| 31R: | CGGGATCCATCGATTGCCTGACCGGCTTCGC | SEQ ID NO: 41 |
| 32F: | GCTCTAGAGGCGCCTCGACCGAAGGCAACGTC | SEQ ID NO: 42 |
| 36F: | GCTCTAGAGGCGGTAGCGGTTCGGAG | SEQ ID NO: 43 |
| 37R: | CGGGATCCGCTAGCCGCTGCGAGCTTGGTC | SEQ ID NO: 44 |
| 38F: | D3: GCTCTAGAGCTAGCGACGAGGGGAAGCAGTC | SEQ ID NO: 45 |
| 39R: | CGGGATCCGCTAGCGGAATGAATGGACGTGACATT | SEQ ID NO: 46 |
| 40F: | GCTCTAGAGCAAGCGCAATCCAGGGAA | SEQ ID NO: 47 |
| 41R: | CGGGATCCGCTAGCCTCGATTCCCGCGAAATT | SEQ ID NO: 48 |
| 44R: | GGAATTCTGTCATGTTTTTGCTCCG | SEQ ID NO: 49 |
| 45F: | GCTCTAGACAATTGCAGTGGAATTTCGCGGGT | SEQ ID NO: 50 |
| 46R: | CGGGATCCCAATTGCTCTGTCATGTTTTTG | SEQ ID NO: 51 |
| 47F: | GCTCTAGACAATTGTGGAATTTCGCGGGTA | SEQ ID NO: 52 |
| 48R: | CGGGATCCCGTACGGTTGCCTTCGGTCGAAGC | SEQ ID NO: 53 |

-continued

| | | |
|---|---|---|
| 49F: | GCTCTAGACGTACGGGGATGTTCGCATAGGGC | SEQ ID NO: 54 |
| 50R: | GGGGTACCAGTGACGTTGCCTTCG | SEQ ID NO: 55 |
| 51F: | GGGGTACCTTCGCATAGGGCAACGCC | SEQ ID NO: 56 |
| 52F: | AAACTGCAGGCATAGGGCAACGCCG | SEQ ID NO: 57 |
| 53R: | CGGGATCCATGCATCCCAGTGACGTTGCC | SEQ ID NO: 58 |
| eGFP-F: | GGACTAGTATGGTGAGCAAGGGCGAGGAGCTG | SEQ ID NO: 59 |
| eGFP-R: | ACGGATCCTTATCTAGATCCGGTGGATCC | SEQ ID NO: 60 |
| ESXA-M1-F: | GACTAGTCCCGGTGAACATACTCATGAC | SEQ ID NO: 61 |
| EsxA-M1-R: | GACTAGTATACAGGCGTGGCACTTTCCTGC | SEQ ID NO: 62 |
| EsxR-F: | GGACTAGTCAGATTATGTACAACTATCCGG | SEQ ID NO: 63 |
| EsxR-R: | GGACTAGTGCCCCACTTGGCGG | SEQ ID NO: 64 |

B. Bioinformatics. Selected sequences taken from the TubercuList server at the Institut Pasteur (http://genolist.pasteur.fr/TubercuList) were screened for the presence of putative coiled-coil motifs using the MultiCoil software available at the Massachusetts Institute of Technology (http://multicoil.lcs.mit.edu/cqi-bin/multicoil). Based on the coiled-coil prediction and available experimental evidence, we used the structure of the four helical-bundle structure of the cytoplasmic domain of a serine chemotaxis receptor (17) to build a model of the ESAT-6 and CFP-10 complex. In this model, the amino acids in position "a" and "d" of the helices in the template were occupied as far as possible by hydrophobic amino acids. In agreement with reported NMR data (19) the two resulting helical hairpins for CFP-10 and ESAT-6 were put side-by-side and antiparallel, with the WXG motif at opposite ends of the complex structure. Structures were refined with a short molecular dynamics/simulated annealing protocol (18), restraining the experimentally known helical elements (Ala 8 to Gln 40 and Ala 46 to Gly 80 for CFP-10; Phe 8 to Trp 43 and Glu 49 to Ala 84 for ESAT-6)(19).

C. Protein Extraction, Column Purification, and Immunoblotting. Cell-free protein extracts were prepared from early log phase cultures of recombinant strains grown in 7H9 or Sauton's media and processed by standard procedures. Culture filtrates were concentrated using a Millipore filter with a 3 kDa cutoff. Western blots and antigen detection were performed as described previously, using anti-ESAT-6 monoclonal antibodies purchased from the Statens Serum Institute (Denmark) and in-house polyclonal antibodies directed against CFP-10 or PPE-68 (12). HIS-tagged proteins were purified using mini-columns containing 80 μl $Ni^{2+}$ NTA agarose. Cell lysates or culture filtrates were passed through the mini-columns then washed with phosphate buffered saline (PBS), (pH 7.3) with 300 mM NaCl and 20 mM Imidazole. Bound protein was eluted with PBS containing 300 mM NaCl and 250 mM Imidazole. Samples were precipitated with 10% TCA, dissolved in PBS and separated by SDS-PAGE (15%), before blotting onto a Nitrocellulose membrane. Monoclonal anti-ESAT-6, anti-HIS or polyclonal CFP-10 antibodies were used for immune-detection.

D. Virulence Studies and Immunological Assays. Virulence and immunological assays were done using SCID mice (IFFA CREDO, France) for intravenous infection and/or C57BL/6 mice for aerosol infection or subcutaneous vaccination as previously described (12-14).

Example 2

Mutation of Conserved Residues of ESAT-6 Identifies Biologically Important Amino Acids Sequence alignment of ESAT-6 orthologs from M. tuberculosis and M. leprae revealed that 33 amino acids are conserved between the two ESAT-6 molecules (FIG. 1A), and 12 of these are also conserved in ESAT-6 like proteins from the phylogenetically more distant species Corynebacterium diphtheriae. Fourteen residues scattered along the M. tuberculosis ESAT-6 molecule were selected for mutation in pRD1-2F9 and the resultant cosmids were integrated into a M. tuberculosis ARD1 strain (H37RvΔRD1)(7). Using our cloning strategy (FIG. 5), recombinant M. tuberculosis strains that expressed ESAT-6 with one or two amino-acid replacements were obtained and screened for secretion of ESAT-6, immunogenicity and virulence (Table 1).

TABLE 1

Characteristics of recombinant M. tuberculosis strains carrying ESTA-6 mutation

| Strain H37RvΔRD1 | Primers | CFP-10 specific IFN-γ responses | ESAT-6 specific IFN-γ responses | Ratio in lungs* | Ratio in spleen* | Virulence |
|---|---|---|---|---|---|---|
| ::pYUB412 | −control | < | < | 6.7 | 23 | A |
| ::2F9 | +control | 13–18 ng/ml | 12–19 ng/ml | 1500 | 24444 | V |
| ::2F9-EsxA-T2H | 1-25-24-8 | 3 ng/ml | 4 ng/ml | 2000 | 40000 | V |
| ::2F9-EsxA-Q4L | 1-44-45-8 | nd | 1.5 ng/ml | 440 | 130 | V |
| ::2F9-EsxA-F8I | 1-23-22-8 | < | < | 17 | 1200 | V |
| ::2F9-EsxA-A14R | 1-41-40-8 | < | < | 21 | 800 | V |

TABLE 1-continued

Characteristics of recombinant *M. tuberculosis* strains carrying ESTA-6 mutation

| Strain H37RvΔRD1 | Primers | CFP-10 specific IFN-γ responses | ESAT-6 specific IFN-γ responses | Ratio in lungs* | Ratio in spleen* | Virulence |
|---|---|---|---|---|---|---|
| ::2F9-EsxA-L28A/L29S | 1-39-38-8 | < | < | 1.7 | 12 | A |
| ::2F9-EsxA-W43R | 1-37-36-8 | < | < | 2 | 3 | A |
| ::2F9-EsxA-G45T | 1-19-18-8 | < | < | 1.1 | 31 | A |
| ::2F9-EsxA-Q55I/Q56A | 1-28-27-8 | 5 ng/ml | 6 ng/ml | 53 | 1400 | V |
| ::2F9-EsxA-N66I/N67A | 1-30-29-8 | < | < | 73 | 620 | V |
| ::2F9-EsxA-M83I | 1-32-31-8 | nd | < | 160 | 350 | V |
| ::2F9-EsxA-V90R | 1-49-48-8 | < | < | 3 | 15 | A |
| ::2F9-EsxA-M93T | 1-51-50-8 | < | nd | 41 | 210 | V |
| ::2F9-EsxA-F94Q | 1-52-53-8 | < | < | 38 | 34 | A |

Figure 1:
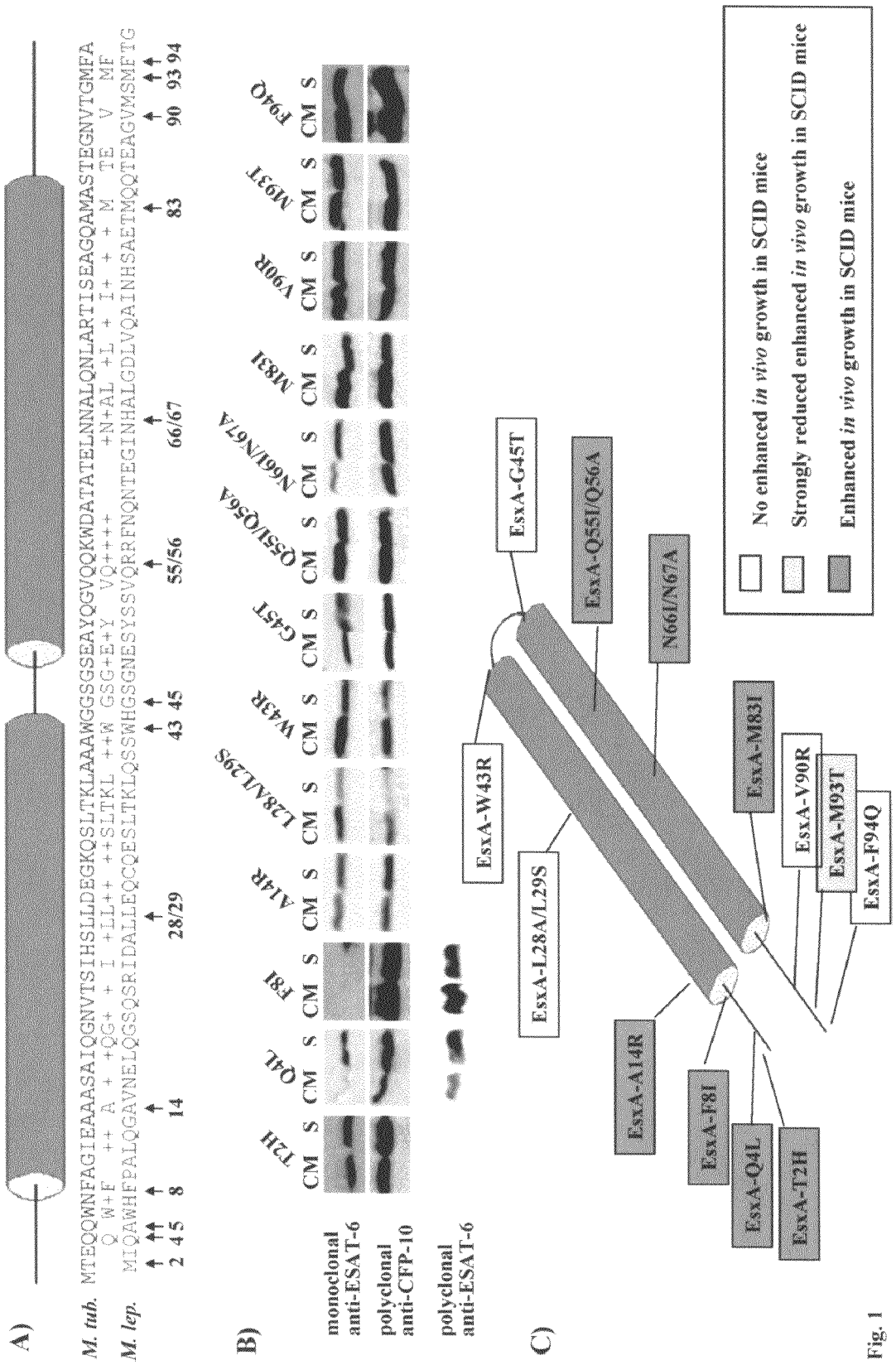
FIG. 1. A) Comparison of ESAT-6 from *M. tuberculosis* (SEQ ID NO: 1) and *M. leprae* (SEQ ID NO: 2). The arrows indicate amino acids that were individually mutated in cosmid pRD1-2F9. B) Immunoblot analysis of the 13 different H37RvΔRD1::2F9EsxA mutant strains, showing the cytosol-membrane (CM) and the supernatant (S) fraction using a monoclonal anti-ESAT-6 antibody. Note that mutation F8I may have changed the recognition site for the monoclonal anti-ESAT-6 antibody. C) Schematic representation of the secondary structure of ESAT-6 (19), and localization of mutations that were studied for their impact on virulence in SCID mice and immunogenicity in C57BL/6 mice.

Table 1. ESAT-6-specific T-cell immunity in C57BL/6 mice immunized with recombinant H37RvDRD1 strains. Concentration of IFN-γ in culture supernatants of splenocytes stimulated ESAT-6: 1–20 peptide. Efficient immunization and specificity of IFN-γ secretion by splenocytes were validated in all cases by stimulation with PPD, as positive control, or MalE: 100–114 peptide, as negative controls, respectively.
< means signal was below detection.
*Virulence in SCID mice, ratio of CFU in spleens or lungs three to four weeks post infection compared to day 0,
V = virulent (enhanced in vivo growth),
A = attenuated (similar to pYUB vector control),
nd = not determined, Among the 13 mutants tested, eight showed different degrees of enhanced in vivo growth after three to four weeks of infection in SCID mice, as witnessed by splenomegaly and high bacterial counts in lungs and spleen, whereas five mutant strains showed characteristics similar to the H37RvΔRD1::YUB412 vector control (FIG. 1C, Table 1). For most samples, the variant ESAT-6 proteins and CFP-10 were found in the culture supernatant (FIG. 1B). We had previously noticed that an enhanced in vivo growth phenotype was only observed when ESAT-6 was secreted. Thus, these findings suggest that loss of virulence in four of the five attenuated mutants is not caused by defective secretion, but rather due to potential loss of interaction with protein partners or putative receptors. For further analysis of these results we used bioinformatic tools. Most interestingly, when we screened ESAT-6 and CFP-10 for the presence of coiled-coil motives using the MultiCoil program (20), a high probability of multimeric coiled-coil formation was found (FIG. 6).

Figure 2:
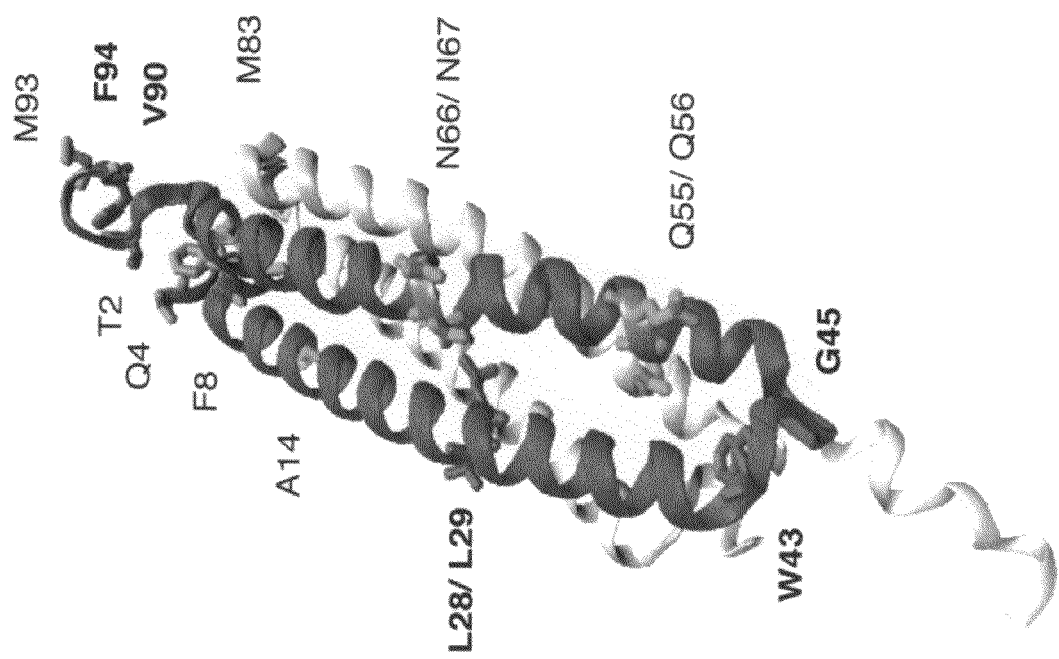
FIG. 2. Model of the ESAT-6/CFP-10 complex, with CFP-10 in white and ESAT-6 in blue. The mutations and their effect are indicated by a color code: red: enhanced virulence abolished; green: enhanced virulence retained. However, note that different degrees of enhanced in vivo growth rates in the various strains were detectable (Table 1).

These observations together with the results from the virulence assay of mutant strains and structural data from the available literature (15, 19, 21), made it possible for us to build a model of the ESAT-6-CFP-10 protein complex, which is crucial for the interpretation of the observed effects of ESAT-6 mutations on virulence. As shown in FIG. 2, mutations that abolish virulence concern residue L29, important for the stability of the hairpin/coiled-coil structure of the molecule, residues W43 and G45 that constitute the loop and contain the conserved WXG motif, as well as residues V90 and F94 in the extreme C-terminal tail. Similarly, M93T, also located in the extreme C-terminus, showed an almost attenuated phenotype. The other tested mutants (T2H, Q4L, F8I, A14R, Q55I/Q56A, N66I/N67A, M83I) did not abolish the virulence of the recombinant *M. tuberculosis* strains in SCID mice as shown by splenomegaly and different degrees of enhanced in vivo growth rates (Table 1). These mutations either affect residues in the N- or C-terminal regions (T2H, Q4L, M83I), are predicted to be at the outer surface of the four-helical bundle structure (A14R, Q56A, N66I, N67A), or are conservative in the sense that the mutated residue can stabilise the structure in a similar way: F8I replaces an aromatic with a hydrophobic residue, Q55I replaces a polar residue in the interior with a hydrophobic residue. In our model, Q55 is mostly surrounded by hydrophobic amino acids, and its replacement by a hydrophobic residue could probably be accommodated by small rearrangements in the structure.

Together, these results suggest that correct ESAT-6/CFP-10 complex formation is an important requirement for full virulence of *M. tuberculosis*. In order to obtain experimental evidence of the protein-protein interaction involved in this process, recombinant BCG strains that expressed and secreted hexahistidine (HIS) tagged ESAT-6 and CFP-10 molecules were genetically engineered.

Example 3

Tagged ESAT-6 and CFP-10 Molecules in BCG Allow Co-Purification of Protein Partners When concentrated culture filtrates of recombinant BCG expressing ESAT-6-HIS at the C-terminus were applied to a Ni$^{2+}$ affinity column, two bands of low molecular weight were visible after elution (FIG. 3A). As shown in FIG. 3B, western blot analyses identified the upper band as CFP-10, and the lower band as ESAT-6-HIS. The two molecules, overexpressed as recombinant proteins by *Escherichia coli* have previously been shown to interact, forming a 1:1 protein complex in in vitro experiments (15, 22). This invention confirms these observations and further demonstrates that in mycobacteria, ESAT-6 and CFP-10 are indeed present as a protein complex. This is the first experimental evidence that these two molecules form a tight complex even after being secreted by their proper secretion machinery.

The same binding behavior was also observed using samples of the cytosolic fraction of BCG::2F9-EsxA-HIS (FIG. 3B), indicating that the two molecules interact already shortly after synthesis. The specificity of this interaction is shown by the results obtained with a C-terminal HIS-tagged ESAT-6 W43R BCG mutant. Most interestingly, for this strain ESAT-6 and CFP-10 are found in the supernatant, but co-purification was no longer possible (FIG. 3C), suggesting that mutation of a single residue, W43R, was sufficient to reduce the affinity between ESAT-6 and CFP-10 in such a way that binding between the two antigens did not occur under the given pH conditions. This finding is also of interest for the interpretation of results obtained by virulence screening of mutant strains. As shown above, mutation W43R was associated with attenuation.

When CFP-10 carrying an N-terminal HIS tag was purified via $Ni^{2+}$ affinity chromatography, ESAT-6 was obtained after elution of bound HIS-CFP-10 (FIGS. 3A, B), though the amounts of ESAT-6 co-purified with CFP-10 were lower. However, this experiment confirmed the strong interaction of these two molecules both in and outside the mycobacterial cell and the utility of the attached HIS-tag for purification of proteins produced by slow growing mycobacteria. Like for the ESAT-6-W43R mutant, a double band was observed for the HIS-tagged molecule, induced by the tag.

Figure 4:
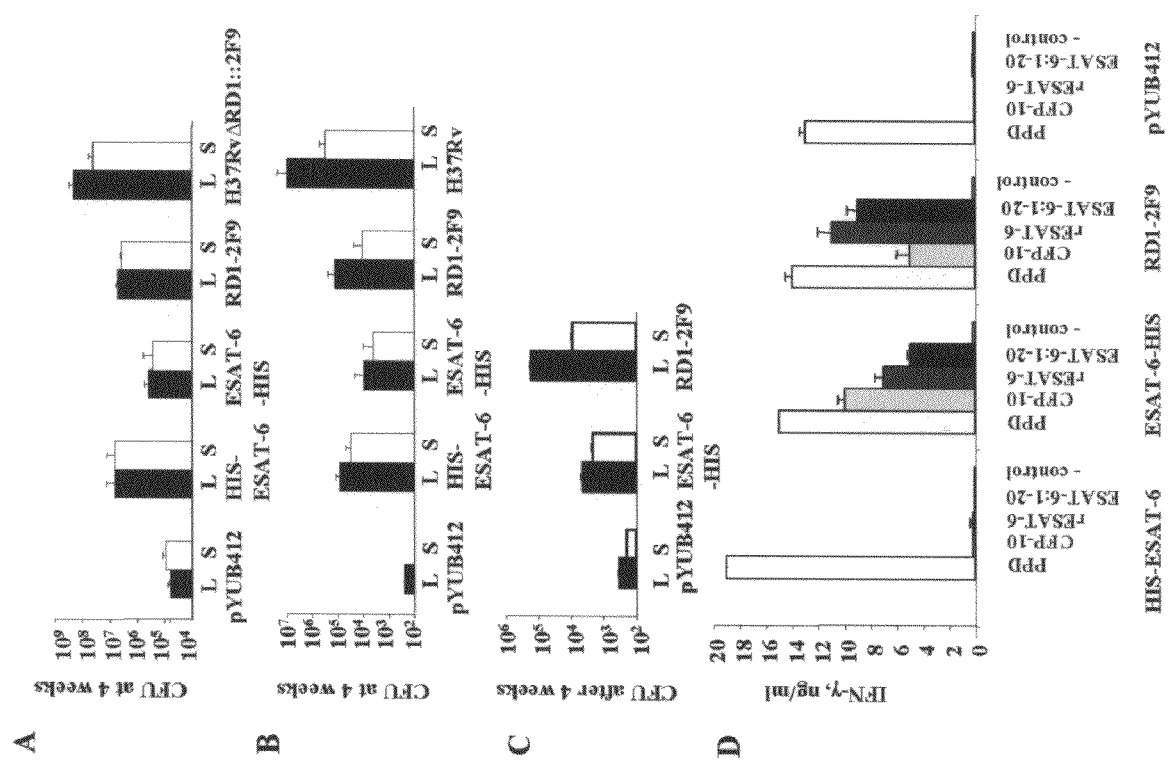
FIG. 4. In vivo growth of different BCG recombinants in mice. A) colony forming units (CFU) in lungs (L) and spleens (S) four weeks after intravenous infection of SCID mice with strains, BCG::2F9-HIS-EsxA (HIS-ESAT-6), BCG::2F9-EsxA-HIS (ESAT-6-HIS), BCG::RD1-2F9 (ESAT-6), H37RvΔRD1::2F9 or BCG vector control (pYUB412). B) CFU in lungs and spleens 4 weeks after aerosol infection of C57BL/6 mice (initial dose: 100 CFU+/−20) with BCG::2F9-HIS-EsxA (HIS-ESAT-6), BCG::2F9-EsxA-HIS (ESAT-6-HIS), BCG::RD1-2F9 (ESAT-6), *M. tuberculosis* H37Rv and BCG vector control (PYUB412). C) CFU in lungs (L) and spleens (S) 4 weeks after intranasal infection of C57BL/6 mice (initial dose: $10^5$ CFU). D) IFN-γ production by splenocytes in response to different antigens after vaccination of C57BL/6 mice with BCG::2F9-HIS-EsxA (HIS-ESAT-6), BCG::2F9-EsxA-HIS (ESAT-6-HIS), BCG::RD1-2F9 (ESAT-6), or BCG::pYUB412 (vector only).

In contrast to the results obtained with the C-terminal HIS tagged ESAT-6, an N-terminal HIS tag for ESAT-6 was not effective for purification of the protein from BCG by $Ni^{2+}$ affinity chromatography (data not shown) as the N-terminal HIS tag had been removed or cleaved from the ESAT-6 molecule in the cytosol, possibly by the action of an endopeptidase (FIG. 7B). Furthermore, ESAT-6 carrying the N-terminal HIS tag did not induce ESAT-6 and CFP-10 specific IFN-γ production by splenocytes of infected mice upon restimulation with the antigen, despite being secreted (FIG. 4). From these experiments we concluded that ESAT-6 with the C-terminal HIS tag resembles native ESAT-6, produced by *M. tuberculosis*, more closely than the N-terminal HIS construct.

Example 4

Larger ESAT-6 Fusion Proteins are Difficult to Transport Outside the Mycobacterial Cell As shown by using hexahistidine tags, modified ESAT-6 proteins containing more amino-acids than the wildtype protein are still secreted by the ESAT-6 system-1. In order to evaluate whether this secretion machinery could be used to export larger fusion proteins, which may be of importance for the development of new recombinant vaccines, we constructed various ESAT-6 protein fusions and tested if they were exported. One of them, ESAT-6 fused at its C-terminus with EsxR (Rv3019c, SwissProt Accession Number: P64093) (EsxA-EsxR) was secreted into the supernatant in sufficient amounts to be detected by Western blotting (FIG. 7D). For this construct, CFP-10 was also found in the supernatant. However, due to the larger size and different structure, much of the fusion protein was retained in the cell wall fraction, where wildtype ESAT-6 was not present (FIG. 7D)

Another recombinant protein, ESAT-6 fused to the ESAT-6 orthologue of *M. leprae* (MLEsxA, SwissProt Accession Number: Q50206), was strongly expressed, but only very little amounts of the protein were detected in the culture supernatant, suggesting that the structural conformation of this fusion protein did not match the requirements of the secretion machinery. As with EsxA-EsxR, the EsxA-MLEsxA fusion protein was present in the cell wall fraction (data not shown). Also constructed was an ESAT-6-C-terminal GFP fusion. There was obtained a recombinant BCG characterized by green fluorescent colonies. Western Blot analysis of the culture supernatant of this recombinant BCG strain showed a large fusion protein that reacted with the ESAT-6 monoclonal antibody and infection of native macrophages revealed that the ESAT-6-GFP-fusion protein was expressed in the engulfed bacteria (FIGS. 7E, F). However, this ESAT-6-GFP fusion protein, that is several times larger than ESAT-6 alone, did not induce ESAT-6 specific T-cell responses in C57BL/6 mice, and did not increase virulence in SCID mice (data not shown), indicating that ESAT-6 fused to GFP had lost its biological function. For this reason, constructs that only contain small tags are better suited to preserve the biological function of the ESAT-6 molecule and still allow specific purification and detection procedures to be employed. In addition to HIS-tag constructs, EsxA-Tetracysteine-tag (FIG. 7G) and/or EsxA-FLAG-tag constructs (data not shown) are useful constructs.

Example 5

Analysis of IFN-γ Responses and Virulence Defines Three Groups of Mutant Strains To monitor the biological effects of the various genetic modifications of ESAT-6, intravenous infection of SCID mice and recording of IFN-γ responses from splenocytes of immuno-competent C57BL/6 mice were used.

It was first observed that the tested strains that induced an IFN-γ response to ESAT-6 were also found to cause splenomegaly and enhanced in vivo growth in SCID mice. However, variation in virulence occurred, as for some strains (e.g. BCG::2F9-EsxA-HIS) growth in SCID mice was less pronounced (Table 1, FIG. 4A). A few selected strains were also tested in immunocompetent C57BL/6 mice by aerosol infection. This approach revealed that strain BCG::2F9-EsxA-HIS Was able to multiply in the lungs of these mice but to a lesser degree than the BCG::RD1-2F9 control and the BCG::2F9-HIS-EsxA (FIG. 4B). As such, the fusion of a HIS tag to the C-terminal end of ESAT-6 (BCG::2F9-EsxA-HIS) resulted in intermediate virulence. The strain, however, retained its capacity to induce IFN-γ responses upon restimulation with ESAT-6 peptides or proteins in C57BL/6 mice (FIG. 4D).

In contrast, the opposite was not always true, as mutants of the second group were virulent in the SCID mouse model, but did not elicit ESAT-6 specific T-cell responses, probably due to changes in the T-cell epitope or conformational changes, possibly interfering with protein processing. Examples of such strains are BCG::2F9-HIS-EsxA, H37RvΔRD1::2F9EsxA-F8I or H37RvΔRD1::2F9EsxA-A14R (Table 1).

The third group of strains was the one, in which mutation of ESAT-6 abolished both, virulence and immunogenicity. This phenomenon was observed for several strains (H37RvΔRD1::2F9EsxA-L28A/L29S, H37RvΔRD1::2F9EsxA-W43R, H37RvΔRD1::2F9EsxA-G45T, and H37RvΔRD1::2F9EsxA-V90R, H37RvΔRD1::2F9EsxA-F94Q). Among these were constructs that had ESAT-6 mutated at the extreme C-terminus (H37RvΔRD1::2F9EsxA-V90R, H37RvΔRD1::2F9EsxA-F94Q). Similar results were obtained with a recombinant BCG strain (BCG::RD1-2F9-esxAA84-95) secreting a C-terminally truncated ESAT-6 protein (FIG. 7C), which did not induce ESX-1 related enhanced virulence nor ESAT-6 specific T-cell responses compared to BCG::RD1-2F9 strain (data not shown).

Example 6

Table 2 is a comparison of ESX-1 specific T-cell immunity (i.e. immunity against ESAT-6 and CFP-10 antigens) and virulence obtained with *M. microti* recombinants containing modified pRD1-2F9 cosmids. Concentration of IFN-γ in culture supernatants of splenocytes that were stimulated with ESAT-6 1-20 peptide, recombinant ESAT6 protein (rESAT-6) or recombinant CFP10 protein (rCFP-10). In all cases efficient immunisation and specificity of IFN-γ secretion by splenocytes was validated with purified protein derivative (PPD)

and MalE:100-114 peptide as positive and negative controls respectively. Results are of at least 2 independent experiments with three mice and are expressed as mean values of duplicate cuture wells. SD values are within 10%. < indicates that the signal was below detection limit (1 ng/ml). Ratio of colony-forming units (CFU) at day 30 relative to initial dose recovered in the lungs and spleen of severe combined immunodeficient mice (SCID) after intravenous infection with $10^6$ CFU.

TABLE 2

| Recombinant strain | Immunogenicity IFNγ (ng/ml) | | | Virulence in SCID mice Ratio of CFU at day 30 relative to day 0 | | Attenuated/ Virulent phenotype |
|---|---|---|---|---|---|---|
| | ESAT-6: 1-20 | r-ESAT-6 | r-CFP-10 | Lungs | Spleen | |
| *M. microti* | | | | | | |
| pYUB412 | 21 | < | < | 4 | 2 | A |
| pRD1-2F9 | 16 | 20 | 17 | 100 | 80 | V |
| Δrv3860-64 | 22 | 17 | 16 | 94 | 26 | V |
| Δrv3860-66 | 12 | 12 | 10 | 14 | 2 | A |

*M. microti* strains containing variants of pRD1-2F9, lacking either rv3860-rv3864 or rv3860-rv3866, clearly secreted ESAT-6 and CFP-10 (Δrv3860-66 shown in FIG. 5A).

Moreover *M. microti* Δrv3860-66 retained antigen specific T-cell immunogenicity (Table 2) but without showing enhanced in vivo growth in SCID mice. Loss of rv3865 and part of rv3866 did not affect ESAT-6 secretion or immunogenicity, but led to attenuation. This suggests that Rv3865 and/or Rv3866 may represent virulence factors independent of ESAT-6 and CFP-10.

In summary, proteins of the 6 kDa (early secreted antigenic target) ESAT-6 secretion system-1 of *Mycobacterium tuberculosis* are not only strongly involved in the anti-mycobacterial Th1-host immune response, but are also key players for virulence. In this invention, protein engineering together with bioinformatic, immunological, and virulence analyses made it possible to pinpoint regions of the ESAT-6 molecule that are critical for its biological activity in *Mycobacterium*. Mutation of the Trp-X-Gly motif, conserved in a wide variety of ESAT-6-like proteins, abolished complex formation with the partner protein CFP-10, induction of specific T-cell responses and virulence. Replacement of conserved Leucine residues interfered with secretion, coiled-coil formation and virulence, whereas certain mutations at the extreme C-terminus did not affect secretion, but caused attenuation, possibly due to altered ESAT-6 targeting or trafficking. In contrast, mutation of several residues on the outer surface of the four-helical bundle structure of the ESAT-6/CFP-10 complex showed much less effects.

Construction of recombinant BCG expressing ESAT-6 with a C-terminal tag made it possible to co-purify ESAT-6 and CFP-10, experimentally confirming their strong interaction in and outside of the mycobacterial cell. These strains induced potent, antigen-specific T-cell responses and intermediate in vivo growth in mice, suggesting that it remained immunogenic and biologically active in spite of the tag. Together with previous NMR data, the results of this invention have allowed a biologically relevant model of the ESAT-6/CFP-10 complex to be constructed that is critical for understanding the structure-function relationship in tuberculosis pathogenesis.

Example 7

Recombinant BCG strains were constructed that carry a modified version of the RD1-2F9 cosmid, previously used for integration of the modified RD1 region into *M. tuberculosis* Delta RD1 (see Brodin et al., J. Biol. Chemistry, 2005, 280: 33953-59.) To obtain the different variants of the pRD1-2F9 cosmid, the previously described procedures were used.

Specifically, 250 to 300 microliters of electrocompetent cells of BCG Pasteur 1173P2, which were obtained by washing and concentrating 7 to 10 days old BCG cultures, were mixed with 5 to 10 microliters of concentrated and dialized miniprep DNA of the modified RD1-2F9 cosmids, and subjected to electroporation as previously described (according to standard procedures described in Pym et al., Mol. Microbiol., 46:709-717, 2002).

The following cosmids were electroporated into BCG and further tested:
  BCG-RD1-ESAT-6-L28A/L29S
  BCG-RD1-ESAT-6-W43R
  BCG-RD1-ESAT-6-G45T
  BCG-RD1-ESAT-6-V90R
  BCG-RD1-ESAT-6-M93T
  BCG-RD1-ESAT-6-HIS.

For aerosol infections of C57BL/6 mice with recombinant BCG strains, 5 ml of a briefly sonicated strain suspension of $5 \times 10^6$ recombinant BCG bacteria was nebulized into containers containing groups of 12 mice, resulting in an average infection dose in the lung of about 10 to 100 CFU. Mice were left for 3 to 4 weeks, and sacrificed. For the first experiment, enumeration of bacteria on plates was rendered difficult due to contamination and dilution/plating problems. Nevertheless, parts of the infected lungs from these experiments, which were fixed in formaldehyde solution, were subjected to histological examination that permitted classification of the samples according to the lesions as follows:
  BCG-RD1-ESAT-6-W43R: Few lesions, congestion minima, some macrophages;
  BCG-RD1-ESAT-6-L28A/L29S: Some granuloma + to ++, lymphocytes and perivascular histiocytes;
  BCG-RD1-ESAT-6-G45T: Granuloma +/−, some lymphocytes and histiocytes;
  BCG-RD1-ESAT-6-V90R: Some infiltrates without real granuloma, minimal lesions;
  BCG-RD1-ESAT-6-M93T: Peribronchic infiltrates and some granuloma; and
  BCG-RD1-2F9: Important granuloma +++, typical for a mycobacterial infection, spumous macrophages, +++ lymphocytes.

Example 8

In a second round of experiments, using an aerosol infection of C57BV6 mice with the same dose as in Example 7, the following strains were tested:

BCG-vector control,
BCG-RD1-ESAT-6-W43R,
BCG-RD1-ESAT-6-L28A/L29S,
BCG-RD1-ESAT-6-HIS,
BCG-RD1-ESAT-6-M93T, and
BCG-RD1-2F9.
Enumeration of the bacterial load after 30 days gave the values shown in FIG. 8.

Examples 7 and 8 show that the recombinant BCG-RD1-ESAT-6-modified strains are less virulent than the BCG::RD1-2F9 control strain, showing at least 1 log less bacteria in the lungs after 30 days than the control. For BCG::RD1-L28A/L29S, no colonies were detected on the corresponding plates for the lung samples obtained at day 30.

Example 9

The six recombinant vaccine strains identified in Example 6 were tested in two rounds of mouse vaccination and challenge studies, using ca. $10^5$ bacteria as subcutaneous inoculum. Two months after vaccination, mice were infected by aerosol (nebulization) with either *M. tuberculosis* strain "Beijing" or H37Rv. Four weeks after the challenge, mice were sacrificed and organs homogenized before being plated out for enumeration, obtaining the results shown in FIGS. 9 and 10.

First round of protection study of recombinant BCG strains in C57BL/6 mice is shown in FIGS. 10(A) and 10(B). The Y axis of the two graphs shows the bacterial charges in CFU in lungs and spleen, respectively.

Second round of the protection study of recombinant BCG strains in C57BL/6 mice is shown in FIGS. 11(A) and 11(B). Once again, the Y axis of the two graphs shows the bacterial charges in CFU in lungs and spleen, respectively.

The two rounds of mouse protection experiments have shown that some of the recombinant BCG::RD1 vaccine strains that express modified ESAT-6 exhibit a better protective efficacy against *M. tuberculosis* that the BCG vector control strains. For example, BCG::RD1-M93T showed better protection in lungs and spleens in both experiments. For BCG::RD1-ESAT-6-HIS, better protection than the BCG control was observed in the lungs (both experiments) and in the spleen in the second experiment. BCG::RD1-L28A/L29S was only tested once and showed improved protection relative to the control. BCG::RD1-W43R and BCG::RD1-G45T showed intermediate efficacy, while BCG::RD1-V90R and BCG::RD1-PPE68ko (containing an intact esxA gene, but having a truncation in the neighboring ppe68 gene) did not show better efficacy than the BCG control strain.

As the BCG::RD1-ESAT-6-HIS strain showed one of the best protective efficacies in the lungs, this strain was further used in a guinea pig vaccination experiment, detailed in Example 10 below.

Example 10

The protective potential of recombinant strain BCG-RD1-ESAT-6-HIS (synonymous to BCG::2F9-EsxA-HIS) was evaluated in the guinea pig model. The conditions of the experiments were very similar to the ones described in Pym et al., Nature Medicine, 2003. In brief, after vaccination with BCG or saline (non-vaccinated control) or BCG::RD1-2F9-EsxA-HIS (synonymous to BCG::RD1-ESAT-6-HIS), the animals were challenged 10 weeks post vaccination with an aerosol of *M. tuberculosis* H37Rv resulting in 500 colony forming units (CFU) in the lungs of the animals. After the challenge, the weight (in grams) was monitored as shown on the Y axis in FIG. 11. Animals that showed a weekly weight loss due to tuberculosis of more than 20% were sacrificed.

The non-vaccinated (saline control) guinea pigs had to be all sacrificed within the first 70 days post challenge due to severe tuberculosis indicated by strong weight loss, as shown on the Y axis in grams in FIG. 11(A). The numbers in the box correspond to the identification names of the various guinea pigs that were tested.

From the 8 BCG-Danish vaccinated guinea pigs, 4 (595A, 464B NC60688, 4075, and 4F6F) had already been sacrificed due to severe tuberculosis indicated by strong weight loss, as shown on the Y axis in grams in FIG. 11(B).

Five of six guinea pigs vaccinated with the recombinant BCG::RD1-ESAT-6-His were still alive at day 150. Only one guinea pig (60707 BK) had to be sacrificed due to weight loss. FIG. 11(C).

FIG. 12 shows the overview of the guinea pig vaccination-challenge experiment, showing that the group of animals vaccinated with BCG::RD1-ESAT-6-His (BCG::2F9-EsxA-His) was best protected, as there was only one guinea pig lost at day 150 post challenge. Apart from the names BCG::2F9-EsxA-His, BCG Danish, and the saline control, the remaining names in the box correspond to the other participants of the experiment.

REFERENCES

The entire disclosures of each of the following publications are relied upon and incorporated by reference herein:

1. Mahairas, G. G., Sabo, P. J., Hickey, M. J., Singh, D. C. & Stover, C. K. (1996) *J Bacteriol* 178, 1274-82.
2. Brodin, P., Eiglmeier, K., Marmiesse, M., Billault, A., Garnier, T., Niemann, S., Cole, S. T. & Brosch, R. (2002) *Infect Immun* 70, 5568-78.
3. Mostowy, S., Cousins, b. & Behr, M. A. (2004) *J Bacteriol* 186, 104-9.
4. Cole, S. T., Brosch, R., Parkhill, J., Garnier, T., Churcher, C., Harris, D., Gordon, S. V., Eiglmeier, K., Gas, S., Barry, C. E., 3rd, Tekaia, F., Badcock, K., Basham, D., Brown, D., Chillingworth, T., Connor, R., Davies, R., Devlin, K., Feltwell, T., Gentles, S., Hamlin, N., Holroyd, S., Hornsby, T., Jagels, K., Barrell, B. G. & et al. (1998) *Nature* 393, 53744.
5. Brosch, R., Gordon, S. V., Marmiesse, M., Brodin, P., Buchrieser, C., Eigimeier, K., Garnier, T., Gutierrez, C., Hewinson, G., Kremer, K., Parsons, L. M., Pym, A. S., Samper, S., van Soolingen, D. & Cole, S. T. (2002) *Proc Natl Acad Sci USA* 12, 12.
6. Lewis, K. N., Liao, R., Guinn, K. M., Hickey, M. J., Smith, S., Behr, M. A. & Sherman, D. R. (2003) *J Infect Dis* 187, 117-23.
7. Hsu, T., Hingley-Wilson, S. M., Chen, B., Chen, M., Dai, A. Z., Morin, P. M., Marks, C. B., Padiyar, J., Goulding, C., Gingery, M., Eisenberg, D., Russell, R. G., Derrick, S. C., Collins, F. M., Morris, S. L., King, C. H. & Jacobs, W. R., Jr. (2003) *Proc Natl Acad Sci USA* 100, 12420-5.
8. Sassetti, C. M. & Rubin, E. J. (2003) *Proc Natl Acad Sci USA* 100, 12989-94.
9. Pym, A. S., Brodin, P., Majlessi, L., Brosch, R., Demangel, C., Williams, A., Griffiths, K. E., Marchal, G., Leclerc, C. & Cole, S. T. (2003) *Nat Med* 9, 533-9,
10. Stanley, S. A., Raghavan, S., Hwang, W. W. & Cox, J. S. (2003) *Proc Natl Acad Sci USA* 100, 13001-6.
11. Guinn, K. I., Hickey, M. J., Mathur, S. K., Zakel, K. L., Grotzke, J. E., Lewinsohn, D. M., Smith, S. & Sherman, D. R. (2004) *Mol Microbiol* 51, 359-70.

12. Pym, A. S., Brodin, P., Brosch, R., Huerre, M. & Cole, S. T. (2002) *Mol Microbiol* 46, 709-17.
13. Brodin, P., Majlessi, L., Brosch, R., Smith, D., Bancroft, G., Clark, S., Williams, A., Leclerc, C. & Cole, S. T. (2004) *J infect Dis* 190, 115-22.
14. Majlessi, L., Brodin, P., Brosch, R., Rojas, M. J., Khun, H., Huerre, M., Cole, S. T. & Leclerc, C. (2005) *J Immunol* 174, 3570-9.
15. Renshaw, P. S., Panagiotidou, P., Whelan, A., Gordon, S. V., Hewinson, R. G., Williamson, R. A. & Carr, M. D. (2002) *J Biol Chem* 277, 21598-603.
16. Pallen, M. J. (2002) *Trends Microbiol* 10, 209-12.
17. Kim, K. K., Yokota, H. & Kim, S. H. (1999) *Nature* 400, 787-92.
18. Nilges, M. & Brunger, A. T. (1991) *Protein Eng* 4, 649-59.
19. Renshaw, P. S., Veverka, V., Kelly, G., Frenkiel, T. A., Williamson, R. A., Gordon, S. V., Glyn Hewinson, R. & Carr, M. D. (2004) *J Biomol NMR* 30, 225-6.
20. Wolf, E., Kim, P. S. & Berger, B. (1997) *Protein Sci* 6, 1179-89.
21. Lightbody, K. L., Renshaw, P. S., Collins, M. L., Wright, R. L., Hunt, D. M., Gordon, S. V., Hewinson, R. G., Buxton, R. S., Williamson, R. A. & Carr, M. D. (2004) *FEMS Microbiol Lett* 238, 255-62.
22. Okkels, L. M. & Andersen, P. (2004) *J Bacteriol* 186, 2487-91.
23. Kwok, S. C. & Hodges, R. S. (2004) *J Biol Chem* 279, 21576-88.
24. Agou, F., Ye, F., Goffinont, S., Courtois, G., Yamaoka, S., Israel, A. & Veron, M. (2002) *J Biol Chem* 277, 17464-75.
25. Pallen, M. J., Dougan, G. & Frankel, G. (1997) *Mol Microbiol* 25, 423-5.
26. Burts, M. L., Williams, W. A., Debord, K. & Missiakas, D. M. (2005) *Proc Natl Acad Sci USA* 102, 1169-74.
27. Horn, C., Namane, A., Pescher, P., Riviere, M., Romain, F., Puzo, G., Barzu, O. & Marchal, G. (1999) *J Biol Chem* 274, 32023-30.
28. Okkels, L. M., Muller, E. C., Schmid, M., Rosenkrands, I., Kaufmann, S. H., Andersen, P. & Jungblut, P. R. (2004) *Proteomics* 4, 2954-60.
29. Polevoda, B. & Sherman, F. (2002) *Genome Biol.* 3, reviews0006 (http://genomebiology.com/).

What is claimed is:

1. A genetically modified strain of *Mycobacterium tuberculosis* complex, wherein the genetically modified strain produces:
   a) at least one polypeptide comprising mutated SEQ ID NO: 1, wherein the mutated SEQ ID NO: 1 has one mutation at L28, and one mutation at L29; or
   b) at least one polypeptide comprising mutated SEQ ID NO: 2, wherein the mutated SEQ ID NO: 2 has one mutation at L27, and one mutation at L28.

2. The genetically modified strain of claim 1, wherein the two mutations in mutated SEQ ID NO: 1 are L28A and L29S.

3. The genetically modified strain of claim 1, wherein the two mutations in mutated SEQ ID NO: 2 are L27A and L28S.

4. The genetically modified strain of claim 1 or 2 or 3, wherein the strain is a *Mycobacterium tuberculosis* strain or a *Mycobacterium bovis* BCG strain, and the polypeptide optionally comprises a hexa-histidine tag, a tetra-cysteine tag, a FLAG-tag, or a GFP polypeptide.

5. A genetically modified strain which is the strains deposited at the Collection Nationale de Cultures de Microorganismes (C.N.C.M.) having Accession No.I.

6. An immunogenic composition comprising a genetically modified strain of claim 1 or 2 or 3 and a pharmaceutically acceptable carrier.

7. A method of modulating an immune response to an infection by a Mycobacterium in a host, wherein the method comprises administering to the host a genetically modified strain of claim 1 or 2 or 3.

8. The method of claim 7, wherein the genetically modified strain of claim 1 or 2 or 3 is administered in an amount sufficient to modulate in the host an immune response to infection by at least one pathogen selected from *M. tuberculosis* and *M. leprae*.

9. A therapeutic method that relies on Th1 mediated immunity, wherein the method comprises administering an effective amount of a genetically modified strain of claim 1 or 2 or 3 to a patient.

10. The therapeutic method of claim 9, wherein the patient has bladder cancer or asthma.

* * * * *

UNITED STATES PATENT AND TRADEMARK OFFICE
CERTIFICATE OF CORRECTION

PATENT NO. : 8,398,991 B2
APPLICATION NO. : 11/455929
DATED : March 19, 2013
INVENTOR(S) : Roland Brosch et al.

It is certified that error appears in the above-identified patent and that said Letters Patent is hereby corrected as shown below:

IN THE CLAIMS:

Claim 5, col. 85, line 21, "Accession No.I." should read --Accession No. I-3461--.

Signed and Sealed this
Fourteenth Day of May, 2013

Teresa Stanek Rea
*Acting Director of the United States Patent and Trademark Office*

SEQUENCE LISTING

<160> NUMBER OF SEQ ID NOS: 73

<210> SEQ ID NO 1
<211> LENGTH: 95
<212> TYPE: PRT
<213> ORGANISM: Mycobacterium tuberculosis

<400> SEQUENCE: 1

```
Met Thr Glu Gln Gln Trp Asn Phe Ala Gly Ile Glu Ala Ala Ala Ser
  1               5                  10                  15

Ala Ile Gln Gly Asn Val Thr Ser Ile His Ser Leu Leu Asp Glu Gly
             20                  25                  30

Lys Gln Ser Leu Thr Lys Leu Ala Ala Ala Trp Gly Gly Ser Gly Ser
         35                  40                  45

Glu Ala Tyr Gln Gly Val Gln Gln Lys Trp Asp Ala Thr Ala Thr Glu
     50                  55                  60

Leu Asn Asn Ala Leu Gln Asn Leu Ala Arg Thr Ile Ser Glu Ala Gly
 65                  70                  75                  80

Gln Ala Met Ala Ser Thr Glu Gly Asn Val Thr Gly Met Phe Ala
                 85                  90                  95
```

<210> SEQ ID NO 2
<211> LENGTH: 95
<212> TYPE: PRT
<213> ORGANISM: Mycobacterium leprae

<400> SEQUENCE: 2

```
Met Ile Gln Ala Trp His Phe Pro Ala Leu Gln Gly Ala Val Asn Glu
  1               5                  10                  15

Leu Gln Gly Ser Gln Ser Arg Ile Asp Ala Leu Leu Glu Gln Cys Gln
             20                  25                  30

Glu Ser Leu Thr Lys Leu Gln Ser Ser Trp His Gly Ser Gly Asn Glu
         35                  40                  45

Ser Tyr Ser Ser Val Gln Arg Arg Phe Asn Gln Asn Thr Glu Gly Ile
     50                  55                  60

Asn His Ala Leu Gly Asp Leu Val Gln Ala Ile Asn His Ser Ala Glu
 65                  70                  75                  80
```

Thr Met Gln Gln Thr Glu Ala Gly Val Met Ser Met Phe Thr Gly
        85                  90                  95

<210> SEQ ID NO 3
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 3
atgacagagc agcagtggaa tttcgcgggt atcgaggccg cggcaagcgc aatccaggga      60
aatgtcacgt ccattcattc cgctagcgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcatag                  288

<210> SEQ ID NO 4
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 4
atgcatgagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcatag                  288

<210> SEQ ID NO 5
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 5
atgacagaat tgcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcatag                  288

<210> SEQ ID NO 6
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 6
atgacagagc agcagtggaa tatcgccggt atcgaggccg cggcaagcgc aatccaggga      60
aatgtcacgt ccattcattc cctccttgac gaggggaagc agtccctgac caagctcgca     120

```
gcggcctggg gcggtagcgg ttcggaggcg taccagggtg tccagcaaaa atgggacgcc      180
acggctaccg agctgaacaa cgcgctgcag aacctggcgc ggacgatcag cgaagccggt      240
caggcaatgg cttcgaccga aggcaacgtc actgggatgt tcgcatag                   288
```

<210> SEQ ID NO 7
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 7

```
atgacagagc agcagtggaa tttcgcgggt atcgaggcta gagcaagcgc aatccaggga       60
aatgtcacgt ccattcattc cctccttgac gaggggaagc agtccctgac caagctcgca      120
gcggcctggg gcggtagcgg ttcggaggcg taccagggtg tccagcaaaa atgggacgcc      180
acggctaccg agctgaacaa cgcgctgcag aacctggcgc ggacgatcag cgaagccggt      240
caggcaatgg cttcgaccga aggcaacgtc actgggatgt tcgcatag                   288
```

<210> SEQ ID NO 8
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 8

```
atgacagagc agcagtggaa tttcgcgggt atcgaggccg cggcaagcgc aatccaggga       60
aatgtcacgt ccattcattc cctccttgac gaggggaagc agtccctgac caagctcgca      120
gcggcctggg gcggtagcgg ttcggaggcg taccagggtg tcatcgccaa atgggacgcc      180
acggctaccg agctgaacaa cgcgctgcag aacctggcgc ggacgatcag cgaagccggt      240
caggcaatgg cttcgaccga aggcaacgtc actgggatgt tcgcatag                   288
```

<210> SEQ ID NO 9
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 9

```
atgacagagc agcagtggaa tttcgcgggt atcgaggccg cggcaagcgc aatccaggga       60
aatgtcacgt ccattcattc cctccttgac gaggggaagc agtccctgac caagctcgca      120
gcggcctggg gcggtagcgg ttcggaggcg taccagggtg tccagcaaaa atgggacgcc      180
acggctaccg agctgatcgc cgcgctgcag aacctggcgc ggacgatcag cgaagccggt      240
caggcaatgg cttcgaccga aggcaacgtc actgggatgt tcgcatag                   288
```

<210> SEQ ID NO 10
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 10

```
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatcg cctcgaccga aggcaacgtc actgggatgt tcgcatag                  288

<210> SEQ ID NO 11
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 11
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actggtacct tcgcatag                  288

<210> SEQ ID NO 12
<211> LENGTH: 360
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 12
cattttggcg aggaaggtaa agagagaaag tagactagta tgcatcatca tcatcatcac      60
gcagagatga agaccgatgc cgctaccctc gcgcaggagg caggtaattt cgagcggatc     120
tccggcgacc tgaaaaccca gatcgaccag gtggagtcga cggcaggttc gttgcagggc     180
cagtggcgcg gcgcggcggg gacggccgcc caggccgcgg tggtgcgctt ccaagaagca     240
gccaataagc agaagcagga actcgacgag atctcgacga atattcgtca ggccggcgtc     300
caatactcga gggccgacga ggagcagcag caggcgctgt cctcgcaaat gggcttctga     360

<210> SEQ ID NO 13
<211> LENGTH: 318
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 13
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcaactag tatggtgagc     300
aagggcgagg agctgttc                                                   318

<210> SEQ ID NO 14
```

<211> LENGTH: 336
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 14

```
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcagggag cttcctgaac     300
tgctgccccg gctgctgcat ggagccgtag gctagt                               336
```

<210> SEQ ID NO 15
<211> LENGTH: 324
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 15

```
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcaactag tcttgtcgtc     300
gtcgtccttg tagtcactag ttag                                            324
```

<210> SEQ ID NO 16
<211> LENGTH: 351
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 16

```
atgacagagc agcagtggaa tttcgcgggt atcgaggccg cggcaagcgc aatccaggga      60
aatgtcacgt ccattcattc cctccttgac gaggggaagc agtccctgac caagctcgca     120
gcggcctggg gcggtagcgg ttcggaggcg taccagggtg tccagcaaaa atgggacgcc     180
acggctaccg agctgaacaa cgcgctgcag aacctggcgc ggacgatcag cgaagccggt     240
caggcaatgg cttcgaccga aggcaacgtc actgggatgt tcgcacatca tcatcatcat     300
cactagacta gtggcaacgc cgagttcgcg tagaatagcg aaacacggga t              351
```

<210> SEQ ID NO 17
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 17

```
atgacagagc agcagtggaa tttcgcgggt atcgaggccg cggcaagcgc aatccaggga      60
```

```
aatgtcacgt ccattcattc cctccttgac gaggggaagc agtccctgac caagctcgca    120
gcggcctggg gcactagtgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgt tcgcatag                288

<210> SEQ ID NO 18
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 18
atgacagagc agcagtggaa tttcgcgggt atcgaggccg cggcaagcgc aatccaggga     60
aatgtcacgt ccattcattc cctccttgac gaggggaagc agtccctgac caagctcgca    120
gcggctagag gcggtagcgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgt tcgcatag                288

<210> SEQ ID NO 19
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 19
atgacagagc agcagtggaa tttcgcgggt atcgaggccg cggcaagcgc aatccaggga     60
aatgtcacgt ccattcattc cgctagcgac gaggggaagc agtccctgac caagctcgca    120
gcggcctggg gcggtagcgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgt tcgcatag                288

<210> SEQ ID NO 20
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 20
atgacagagc agcagtggaa tttcgcgggt atcgaggccg cggcaagcgc aatccaggga     60
aatgtcacgt ccattcattc cctccttgac gaggggaagc agtccctgac caagctcgca    120
gcggcctggg gcggtagcgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgc aggcatag                288

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 21
ggaattccgt taacacgctt ttcgagag                                        28

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgggatccac tagtcatgtt tttgctccgt ttc                                  33

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctctagact agtcatcatc atcatcatca cgagcagcag tggaatttcg c              51

<210> SEQ ID NO 24
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgggatccac tagtctagtg atgatgatga tgatgtgcga acatcccagt gacg           54

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gctctagact agtggcaacg ccgagttcgc g                                    31

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccaagcttg gccggaagag cttgtcg                                         27

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
```

-continued cgggatccac tagtctactt tctctctttt acc                                    32

<210> SEQ ID NO 28
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gctctagact agtatgcatc atcatcatca tcacgcagag atgaagaccg atgccg          56

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cgggatccac tagttgcgaa catcccagtg acg                                   33

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gctctagact agttagggca acgccgagtt cgcg                                  34

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gctctagact atggttcgga ggcgtacc                                         28

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
cgggatccac tagtgcccca ggccgctgcg                                       30

<210> SEQ ID NO 33
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gctctagagg cgccggtatc gaggccgcgg c                                     31

```
<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgggatcccg atcgatattc cactgctgct ctgt                              34

<210> SEQ ID NO 35
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gctctagaat gcatgagcag cagtggaatt tcg                               33

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgggatcccg atgcatgttt ttgctccgtt tctt                              34

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gctctagagg cgccaaatgg gacgccacgg ctac                              34

<210> SEQ ID NO 38
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cgggatccat cgatgacacc ctggtacgcc tc                                32

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgggatccat cgatcagctc ggtagccgtg gcg                               33

<210> SEQ ID NO 40
```

<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
gctctagagc gccgcgctgc agaacctggc         30

<210> SEQ ID NO 41
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
cgggatccat cgattgcctg accggcttcg c         31

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
gctctagagg cgcctcgacc gaaggcaacg tc         32

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
gctctagagg cggtagcggt tcggag         26

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 44
cgggatccgc tagccgctgc gagcttggtc         30

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
gctctagagc tagcgacgag gggaagcagt c         31

<210> SEQ ID NO 46
<211> LENGTH: 35
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 46
cgggatccgc tagcggaatg aatggacgtg acatt                               35

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gctctagagc aagcgcaatc cagggaa                                        27

<210> SEQ ID NO 48
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cgggatccgc tagcctcgat tcccgcgaaa tt                                  32

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ggaattctgt catgttttg ctccg                                           25

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gctctagaca attgcagtgg aatttcgcgg gt                                  32

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cgggatccca attgctctgt catgttttg                                      30

<210> SEQ ID NO 52
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 52
gctctagaca attgtggaat ttcgcgggta                                    30

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cgggatcccg tacggttgcc ttcggtcgaa gc                                 32

<210> SEQ ID NO 54
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gctctagacg tacggggatg ttcgcatagg gc                                 32

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggggtaccag tgacgttgcc ttcg                                          24

<210> SEQ ID NO 56
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggggtaccct cgcatagggc aacgcc                                        26

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aaactgcagg catagggcaa cgccg                                         25

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 58
cgggatccat gcatcccagt gacgttgcc                                          29

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggactagtat ggtgagcaag ggcgaggagc tg                                      32

<210> SEQ ID NO 60
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
acggatcctt atctagatcc ggtggatcc                                          29

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gactagtccc ggtgaacata ctcatgac                                           28

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gactagtata caggcgtggc actttcctgc                                         30

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ggactagtca gattatgtac aactatccgg                                         30

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
```

```
ggactagtgc cccacttggc gg                                              22

<210> SEQ ID NO 65
<211> LENGTH: 26379
<212> TYPE: DNA
<213> ORGANISM: Mycobacterium tuberculosis

<400> SEQUENCE: 65
atgtgatcgc ggcgcgcgac ggcgacatgc tggtgctgca gttggtggcg ccgcaggtcg      60
gcttggcggg catggtgaca gcggtgctgg ggcccgccga acccgccaac gtcgaacccc     120
tgacgggtgt ggcaaccgag ctagccgaat gcacaaccgc gtcccaattg acgcaatacg     180
gtatcgcacc ggcctcggcc cgcgtctatg ccgagatcgt gggtaacccg accggctggg     240
tggagatcgt tgccagccaa cgccaccccg gcggcaccac gacgcagacc gacgccgccg     300
ctggcgtcct ggactccaag ctcggtaggc tggtgtcgct ccccgccgt gttggaggcg      360 acctgtacgg aagcttcctg cccggcactc agcagaactt ggagcgtgcg ctggacggct     420
tgctagagct gctccctgcg ggcgcttggc tagatcacac ctcagatcac gcacaagcct     480
cctcccgagg ctgaccctc acatctccgc tacgacttca gaaagggacg ccatggtgga     540
cccgccgggc aacgacgacg accacggtga tctcgacgcc ctcgatttct ccgccgccca     600
caccaacgag gcgtcgccgc tggacgcctt agacgactat gccggtgc agaccgatga      660 cgccgaaggc gacctggacg ccctccatgc gctcaccgaa cgcgacgagg agccggagct     720
ggagttgttc acggtgacca accctcaagg gtcggtgtcg gtctcaaccc tgatggacgg     780
cagaatccag cacgtcgagc tgacggacaa ggcgaccagc atgtccgaag cgcagctggc     840
cgacgagatc ttcgttattg ccgatctggc ccgccaaaag gcgcgggcgt cgcagtacac     900
gttcatggtg gagaacatcg gtgaactgac cgacgaagac gcagaaggca gcgccctgct     960
gcgggaattc gtggggatga ccctgaatct gccgacgccg gaagaggctg ccgcagccga    1020
agccgaagtg ttcgccaccc gctacgatgt cgactacacc tcccggtaca aggccgatga    1080
ctgatcgctt ggccagtctg ttcgaaagcg ccgtcagcat gttgccgatg tcggaggcgc    1140
ggtcgctaga tctgttcacc gagatcacca actacgacga atccgcttgc gacgcatgga    1200
tcggccggat ccggtgtggg gacaccgacc gggtgacgct gtttcgcgcc tggtattcgc    1260
gccgcaattt cggacagttg tcgggatcgg tccagatctc gatgagcacg ttaaacgcca    1320
ggattgccat cgggggctg tacggcgata tcacctaccc ggtcacctcg ccgctagcga     1380
tcaccatggg ctttgccgca tgcgaggcag cgcaaggcaa ttacgccgac gccatggagg    1440
ccttagaggc cgccccggtc gcgggttccg agcacctggt ggcgtggatg aaggcggttg    1500
tctacggcgc ggccgaacgc tggaccgacg tgatcgacca ggtcaagagt gctggaaat     1560 ggccggacaa gttttggcc ggcgcggccg gtgtggcgca cggggttgcc gcggcaaacc     1620
tggccttgtt caccgaagcc gaacgccgac tcaccgaggc caacgactcg cccgccggtg    1680
aggcgtgtgc gcgcgccatc gcctggtatc tggcgatggc acggcgcagc cagggcaacg    1740
aaagcgccgc ggtggcgctg ctggaatggt tacagaccac tcaccccgag cccaaagtgg    1800
ctgcggcgct gaaggatccc tcctaccggc tgaagacgac caccgccgaa cagatcgcat    1860
cccgcgccga tccctgggat ccgggcagtg tcgtgaccga caactccggc cgggagcggc    1920
tgctccgcga ggcccaagcc gaactcgacc gccaaattgg gctcacccgg gttaaaaatc    1980
agattgaacg ctaccgcgcg gcgacgctga tggcccgggt ccgcgccgcc aagggtatga    2040
aggtcgccca gcccagcaag cacatgatct tcaccggacc gccggtacc ggcaagacca      2100
```

```
cgatcgcgcg ggtggtggcc aatatcctgg ccggcttagg cgtcattgcc gaacccaaac    2160
tcgtcgagac gtcgcgcaag gacttcgtcg ccgagtacga ggggcaatcg gcggtcaaga    2220
ccgctaagac gatcgatcag gcgctgggcg gggtgctttt catcgacgag gcttatgcgc    2280
tggtgcagga aagagacggc cgcaccgatc cgttcggtca agaggcgctg gacacgctgc    2340
tggcgcggat ggagaacgac cgggaccggc tggtggtgat catcgccggg tacagctccg    2400
acatagatcg gctgctggaa accaacgagg gtctgcggtc gcggttcgcc actcgcatcg    2460
agttcgacac ctattccccc gaggaactcc tcgagatcgc caacgtcatt gccgctgctg    2520
atgattcggc gttgaccgca gaggcggccg agaactttct tcaggccgcc aagcagttgg    2580
agcagcgcat gttgcgcggc cggcgcgccc tggacgtcgc cggcaacggt cggtatgcgc    2640
gccagctggt ggaggccagc gagcaatgcc gggacatgcg tctagcccag gtcctcgata    2700
tcgacaccct cgacgaagac cggcttcgcg agatcaacgg ctcagatatg gcggaggcta    2760
tcgccgcggt gcacgcacac ctcaacatga gagaatgaac tatggggctt cgcctcacca    2820
ccaaggttca ggttagcggc tggcgttttc tgctgcgccg gctcgaacac gccatcgtgc    2880
gccgggacac ccgatgtttt gacgaccgcg tgcagttcta cagccgctcg atcgctcttg    2940
gcatcgtcgt cgcggtcctg attctggcgg gtgccgcgct gctggcgtac ttcaaaccac    3000
aaggcaaact cggcggcacc agcctgttca ccgaccgcgc gaccaaccag ctttacgtgc    3060
tgctgtccgg acagttgcat ccggtctaca acctgacttc ggcgcggctg gtgctgggca    3120
atccggccaa cccggccacc gtgaagtcct ccgaactgag caagctgccg atgggccaga    3180
ccgttggaat ccccggcgcc ccctacgcca cgcctgtttc ggcgggcagc acctcgatct    3240
ggaccctatg cgacaccgtc gcccgagccg actccacttc cccggtagtg cagaccgcgg    3300
tcatcgcgat gccgttggag atcgatgctt cgatcgatcc gctccagtca cacgaagcgg    3360
tgctggtgtc ctaccagggc gaaacctgga tcgtcacaac taaggacgc cacgccatag    3420 atctgaccga ccgcgccctc acctcgtcga tggggatacc ggtgacggcc aggccaaccc    3480
cgatctcgga gggcatgttc aacgcgctgc ctgatatggg gccctggcag ctgccgccga    3540
taccggcggc gggcgcgccc aattcgcttg gcctacctga tgatctagtg atcggatcgg    3600
tcttccagat ccacaccgac aagggcccgc aatactatgt ggtgctgccc gacggcatcg    3660
cgcaggtcaa cgcgacaacc gctgcggcgc tgcgcgccac ccaggcgcac gggctggtcg    3720
cgccaccggc aatggtgccc agtctggtcg tcagaatcgc cgaacgggta taccctcac    3780 cgctacccga tgaaccgctc aagatcgtgt cccggccgca ggatcccgcg ctgtgctggt    3840
catggcaacg cagcgccggc gaccagtcgc cgcagtcaac ggtgctgtcc ggccggcatc    3900
tgccgatatc gccctcagcg atgaacatgg ggatcaagca gatccacggg acggcgaccg    3960
tttacctcga cggcggaaaa ttcgtggcac tgcaatcccc cgatcctcga tacaccgaat    4020
cgatgtacta catcgatcca cagggcgtgc gttatggggt gcctaacgcg gagacagcca    4080
agtcgctggg cctgagttca ccccaaaacg cgccctggga gatcgttcgt ctcctggtcg    4140
acggtccggt gctgtcgaaa gatgccgcac tgctcgagca cgacacgctg cccgctgacc    4200
ctagcccccg aaaagttccc gccggagcct ccggagcccc ctgatgacga ccaagaagtt    4260
cactcccacc attacccgtg gccccgggtt gaccccgggc gagatcagcc tcacgccgcc    4320
cgatgacctg gcatcgacga tcccaccgtc gggcgtccaa aagatccttc cctacgtgat    4380
gggtggcgcc atgctcggca tgatcgccat catggtggcc ggcggcacca ggcagctgtc    4440
gccgtacatg ttgatgatgc cgctgatgat gatcgtgatg atggtcggcg gtctggccgg    4500
```

```
tagcaccggt ggtggcggca agaaggtgcc cgaaatcaac gccgaccgca aggagtacct   4560
gcggtatttg gcaggactac gcacccgagt gacgtcctcg gccacctctc aggtggcgtt   4620
cttctcctac cacgcaccgc atcccgagga tctgttgtcg atcgtcggca cccaacggca   4680
gtggtcccgg ccggccaacg ccgacttcta tgcggccacc cgaatcggta tcggtgacca   4740
gccggcggtg gatcgattat tgaagccggc cgtcggcggg gagttggccg ccgccagcgc   4800
agcacctcag ccgttcctgg agccggtcag tcatatgtgg gtggtcaagt ttctacgaac   4860
ccatggattg atccatgact gcccgaaact gctgcaactc cgtacctttc cgactatcgc   4920
gatcggcggg gacttggcgg gggcagccgg cctgatgacg gcgatgatct gtcacctagc   4980
cgtgttccac ccaccggacc tgctgcagat ccgggtgctc accgaggaac ccgacgaccc   5040
cgactggtcc tggctcaaat ggcttccgca cgtacagcac cagaccgaaa ccgatgcggc   5100
cgggtccacc cggctgatct tcacgcgcca ggaaggtctg tcggacctgg ccgcgcgcgg   5160
gccacacgca cccgattcgc ttcccggcgg ccccctacgta gtcgtcgtcg acctgaccgg   5220
cggcaaggct ggattcccgc cgacggtag ggccggtgtc acggtgatca cgttgggcaa   5280
ccatcgcggg tcgcctacc gcatcagggt gcacgaggat gggacggctg atgaccggct   5340
ccctaaccaa tcgtttcgcc aggtgacatc ggtcaccgat cggatgtcgc cgcagcaagc   5400
cagccgtatc gcgcgaaagt tggccggatg gtccatcacg gcaccatcc tcgacaagac   5460 gtcgcgggtc cagaagaagg tggccaccga ctggcaccag ctggtcggtg cgcaaagtgt   5520
cgaggagata acaccttccc gctggaggat gtacaccgac accgaccgtg accggctaaa   5580
gatcccgttt ggtcatgaac taaagaccgg caacgtcatg tacctggaca tcaaagaggg   5640
cgcggaattc ggcgccggac cgcacggcat gctcatcggg accacgggt ctgggaagtc   5700 cgaattcctg cgcacccctga tcctgtcgct ggtggcaatg actcatccag atcaggtgaa   5760
tctcctgctc accgacttca aaggtggttc aaccttcctg ggaatggaaa agcttccgca   5820
cactgccgct gtcgtcacca acatggccga ggaagccgag ctcgtcagcc ggatgggcga   5880
ggtgttgacc ggagaactcg atcggcgcca gtcgatcctc cgacaggccg ggatgaaagt   5940
cggcgcggcc ggagccctgt ccggcgtggc cgaatacgag aagtaccgcg aacgcggtgc   6000
cgacctaccc ccgctgccaa cgcttttcgt cgtcgtcgac gagttcgccg agctgttgca   6060
gagtcacccg gacttcatcg gctgttcga ccggatctgc cgcgtcgggc ggtcgctgag   6120
ggtccatctg ctgctggcta cccagtcgct gcagaccggc ggtgttcgca tcgacaaact   6180
ggagccaaac ctgacatatc gaatcgcatt gcgcaccacc agctctcatg aatccaaggc   6240
ggtaatcggc acaccggagg cgcagtacat caccaacaag gagagcggtg tcgggtttct   6300
ccgggtcggc atggaagacc cggtcaagtt cagcaccttc tacatcagtg gccatacat   6360 gccgccggcg gcaggcgtcg aaaccaatgg tgaagccgga gggcccggtc aacagaccac   6420
tagacaagcc gcgcgcattc acaggttcac cgcggcaccg gttctcgagg aggcgccgac   6480
accgtgaccc gcgccggcga cgatgcaaag cgcagcgatg aggaggagcg cgccaacgg   6540 cccgcgccgg cgacgatgca aagcgcagcg atgaggagga cgcgcgcgca tgactgctga   6600
accggaagta cggacgctgc gcgaggttgt gctggaccag ctcggcactg ctgaatcgcg   6660
tgcgtacaag atgtggctgc cgccgttgac caatccggtc ccgctcaacg agctcatcgc   6720
ccgtgatcgg cgacaacccc tgcgatttgc cctggggatc atggatgaac cgcgccgcca   6780
tctacaggat gtgtggggcg tagacgtttc cggggccggc ggcaacatcg gtattggggg   6840
cgcacctcaa accgggaagt cgacgctact gcagacgatg gtgatgtcgg ccgccgccac   6900
```

```
acactcaccg cgcaacgttc agttctattg catcgaccta ggtggcggcg ggctgatcta   6960
tctcgaaaac cttccacacg tcggtggggt agccaatcgg tccgagcccg acaaggtcaa   7020
ccgggtggtc gcagagatgc aagccgtcat gcggcaacgg gaaaccacct tcaaggaaca   7080
ccgagtgggc tcgatcggga tgtaccggca gctgcgtgac gatccaagtc aacccgttgc   7140
gtccgatcca tacggcgacg tctttctgat catcgacgga tggcccggtt ttgtcggcga   7200
gttccccgac cttgagggc aggttcaaga tctggccgcc caggggctgg cgttcggcgt   7260
ccacgtcatc atctccacgc cacgctggac agagctgaag tcgcgtgttc gcgactacct   7320
cggcaccaag atcgagttcc ggcttggtga cgtcaatgaa acccagatcg accggattac   7380
ccgcgagatc ccggcgaatc gtccgggtcg ggcagtgtcg atggaaaagc accatctgat   7440
gatcggcgtg cccaggttcg acggcgtgca cagcgccgat aacctggtgg aggcgatcac   7500
cgcgggggtg acgcagatcg cttcccagca caccgaacag gcacctccgg tgcgggtcct   7560
gccggagcgt atccacctgc acgaactcga cccgaacccg ccgggaccag agtccgacta   7620
ccgcactcgc tgggagattc cgatcggctt gcgcgagacg gacctgacgc cggctcactg   7680
ccacatgcac acgaacccgc acctactgat cttcggtgcg ccaaatcgg gcaagacgac   7740 cattgcccac gcgatcgcgc gcgccatttg tgcccgaaac agtccccagc aggtgcggtt   7800
catgctcgcg gactaccgct cgggcctgct ggacgcggtg ccggacaccc atctgctggg   7860
cgccggcgcg atcaaccgca acagcgcgtc gctagacgag gccgttcaag cactggcggt   7920
caacctgaag aagcggttgc cgccgaccga cctgacgacg gcgcagctac gctcgcgttc   7980
gtggtggagc ggatttgacg tcgtgcttct ggtcgacgat tggcacatga tcgtgggtgc   8040
cgccgggggg atgccgccga tggcaccgct ggccccgtta ttgccggcgg cggcagatat   8100
cgggttgcac atcattgtca cctgtcagat gagccaggct tacaaggcaa ccatggacaa   8160
gttcgtcggc gccgcattcg ggtcgggcgc tccgacaatg ttcctttcgg gcgagaagca   8220
ggaattccca tccagtgagt tcaaggtcaa gcggcgcccc cctggccagg catttctcgt   8280
ctcgccagac ggcaaagagg tcatccaggc cccctacatc gagcctccag aagaagtgtt   8340
cgcagcaccc ccaagcgccg gttaagatta tttcattgcc ggtgtagcag acccgagct   8400 cagcccggta atcgagttcg ggcaatgctg accatcgggt ttgtttccgg ctataaccga   8460
acggtttgtg tacgggatac aaatacaggg agggaagaag taggcaaatg gaaaaaatgt   8520
cacatgatcc gatcgctgcc gacattggca cgcaagtgag cgacaacgct ctgcacggcg   8580
tgacggccgg ctcgacggcg ctgacgtcgg tgaccgggct ggttcccgcg ggggccgatg   8640
aggtctccgc ccaagcggcg acggcgttca tcggagggg catccaattg ctggcttcca   8700
atgcatcggc ccaagaccag ctccaccgtg cgggcgaagc ggtccaggac gtcgcccgca   8760
cctattcgca aatcgacgac ggcgccgccg cgtcttcgc cgaataggcc cccaacacat   8820
cggagggagt gatcaccatg ctgtggcacg caatgccacc ggagctaaat accgcacggc   8880
tgatggccgg cgcgggtccg gctccaatgc ttgcggcggc cgcgggatgg cagacgcttt   8940
cggcggctct ggacgctcag gccgtcgagt tgaccgcgcg cctgaactct ctgggagaag   9000
cctggactgg aggtggcagc gacaaggcgc ttgcggctgc aacgccgatg gtggtctggc   9060
tacaaaccgc gtcaacacag gccaagaccc gtgcgatgca ggcgacggcg caagccgcg   9120 catacaccca ggccatggcc acgacgccgt cgctgccgga gatcgccgcc aaccacatca   9180
cccaggccgt ccttacggcc accaacttct tcggtatcaa cacgatcccg atcgcgttga   9240
ccgagatgga ttatttcatc cgtatgtgga accaggcagc cctggcaatg gaggtctacc   9300
```

```
aggccgagac cgcggttaac acgcttttcg agaagctcga gccgatggcg tcgatccttg   9360
atcccggcgc gagccagagc acgacgaacc cgatcttcgg aatgccctcc cctggcagct   9420
caacaccggt tggccagttg ccgccggcgg ctacccagac cctcggccaa ctgggtgaga   9480
tgagcggccc gatgcagcag ctgacccagc cgctgcagca ggtgacgtcg ttgttcagcc   9540
aggtgggcgg caccggcggc ggcaacccag ccgacgagga agccgcgcag atgggcctgc   9600
tcggcaccag tccgctgtcg aaccatccgc tggctggtgg atcaggcccc agcgcgggcg   9660
cgggcctgct gcgcgcggag tcgctacctg gcgcaggtgg gtcgttgacc cgcacgccgc   9720
tgatgtctca gctgatcgaa aagccggttg ccccctcggt gatgccggcg gctgctgccg   9780
gatcgtcggc gacgggtggc gccgctccgg tgggtgcggg agcgatgggc cagggtgcgc   9840
aatccggcgg ctccaccagg ccgggtctgg tcgcgccggc accgctcgcg caggagcgtg   9900
aagaagacga cgaggacgac tgggacgaag aggacgactg gtgagctccc gtaatgacaa   9960
cagacttccc ggccacccgg gccggaagac ttgccaacat tttggcgagg aaggtaaaga  10020
gagaaagtag tccagcatgg cagagatgaa gaccgatgcc gctaccctcg cgcaggaggc  10080
aggtaatttc gagcggatct ccggcgacct gaaaacccag atcgaccagg tggagtcgac  10140
ggcaggttcg ttgcagggcc agtggcgcgg cgcggcgggg acggccgccc aggccgcggt  10200
ggtgcgcttc caagaagcag ccaataagca gaagcaggaa ctcgacgaga tctcgacgaa  10260
tattcgtcag gccggcgtcc aatactcgag ggccgacgag gagcagcagc aggcgctgtc  10320
ctcgcaaatg ggcttctgac ccgctaatac gaaaagaaac ggagcaaaaa catgacagag  10380
cagcagtgga atttcgcggg tatcgaggcc gcggcaagcg caatccaggg aaatgtcacg  10440
tccattcatt ccctccttga cgaggggaag cagtccctga ccaagctcgc agcggcctgg  10500
ggcggtagcg gttcggaggc gtaccagggt gtccagcaaa aatgggacgc cacggctacc  10560
gagctgaaca acgcgctgca gaacctggcc cggacgatca gcgaagccgg tcaggcaatg  10620
gcttcgaccg aaggcaacgt cactgggatg ttcgcatagg caacgccga gttcgcgtag  10680 aatagcgaaa cacgggatcg ggcgagttcg accttccgtc ggtctcgccc tttctcgtgt  10740
ttatacgttt gagcgcactc tgagaggttg tcatggcggc cgactacgac aagctcttcc  10800
ggccgcacga aggtatggaa gctccggacg atatggcagc gcagccgttc ttcgacccca  10860
gtgcttcgtt tccgccggcg cccgcatcgg caaacctacc gaagcccaac ggccagactc  10920
cgcccccgac gtccgacgac ctgtcggagc ggttcgtgtc ggccccgccg ccgcccacccc  10980 cacccccacc tccgcctccg ccaactccga tgccgatcgc cgcaggagag ccgccctcgc  11040
cggaaccggc cgcatctaaa ccacccacac ccccatgcc catcgccgga cccgaaccgg  11100
ccccacccaa accacccaca cccccatgc ccatcgccgg acccgaaccg ccccaccca  11160 aaccacccac acctccgatg cccatcgccg gacctgcacc caccccaacc gaatcccagt  11220
tggcgccccc cagaccaccg acaccacaaa cgccaaccgg agcgccgcag caaccggaat  11280
caccggcgcc ccacgtaccc tcgcacgggc cacatcaacc ccggcgcacc gcaccagcac  11340
cgccctgggc aaagatgcca atcggcgaac ccccgcccgc tccgtccaga ccgtctgcgt  11400
ccccggccga accaccgacc cggcctgccc cccaacactc ccgacgtgcg cgccggggtc  11460
accgctatcg cacagacacc gaacgaaacg tcggaaggt agcaactggt ccatccatcc  11520
aggcgcggct gcgggcagag gaagcatccg gcgcgcagct cgcccccgga acggagccct  11580
cgccagcgcc gttgggccaa ccgagatcgt atctggctcc gccacccgc cccgcgccga  11640 cagaacctcc ccccagcccc tcgccgcagc gcaactccgg tcggcgtgcc gagcgacgcg  11700
```

```
tccaccccga tttagccgcc caacatgccg cggcgcaacc tgattcaatt acggccgcaa    11760
ccactggcgg tcgtcgccgc aagcgtgcag cgccggatct cgacgcgaca cagaaatcct    11820
taaggccggc ggccaagggg ccgaaggtga agaaggtgaa gccccagaaa ccgaaggcca    11880
cgaagccgcc caaagtggtg tcgcagcgcg gctggcgaca ttgggtgcat gcgttgacgc    11940
gaatcaacct gggcctgtca cccgacgaga agtacgagct ggacctgcac gctcgagtcc    12000
gccgcaatcc ccgcgggtcg tatcagatcg ccgtcgtcgg tctcaaaggt ggggctggca    12060
aaaccacgct gacagcagcg ttggggtcga cgttggctca ggtgcgggcc gaccggatcc    12120
tggctctaga cgcggatcca ggcgccggaa acctcgccga tcgggtaggg cgacaatcgg    12180
gcgcgaccat cgctgatgtg cttgcagaaa aagagctgtc gcactacaac gacatccgcg    12240
cacacactag cgtcaatgcg gtcaatctgg aagtgctgcc ggcaccggaa tacagctcgg    12300
cgcagcgcgc gctcagcgac gccgactggc atttcatcgc cgatcctgcg tcgaggtttt    12360
acaacctcgt cttggctgat tgtggggccg gcttcttcga cccgctgacc cgcggcgtgc    12420
tgtccacggt gtccggtgtc gtggtcgtgg caagtgtctc aatcgacggc gcacaacagg    12480
cgtcggtcgc gttggactgg ttgcgcaaca acggttacca agatttggcg agccgcgcat    12540
gcgtggtcat caatcacatc atgccgggag aacccaatgt cgcagttaaa gacctggtgc    12600
ggcatttcga acagcaagtt caacccgccc gggtcgtggt catgccgtgg acaggcaca     12660 ttgcggccgg aaccgagatt tcactcgact tgctcgaccc tatctacaag cgcaaggtcc    12720
tcgaattggc cgcagcgcta tccgacgatt tcgagagggc tggacgtcgt tgagcgcacc    12780
tgctgttgct gctggtccta ccgccgcggg ggcaaccgct gcgcggcctg ccaccacccg    12840
ggtgacgatc ctgaccggca gacggatgac cgatttggta ctgccagcgg cggtgccgat    12900
ggaaacttat attgacgaca ccgtcgcggt gctttccgag gtgttggaag acacgccggc    12960
tgatgtactc ggcggcttcg actttaccgc gcaaggcgtg tgggcgttcg ctcgtcccgg    13020
atcgccgccg ctgaagctcg accagtcact cgatgacgcc ggggtggtcg acgggtcact    13080
gctgactctg tgtcagtca gtcgcaccga gcgctaccga ccgttggtcg aggatgtcat    13140
cgacgcgatc gccgtgcttg acgagtcacc tgagttcgac cgcacggcat tgaatcgctt    13200
tgtgggggcg gcgatcccgc ttttgaccgc gcccgtcatc gggatggcga tgcgggcgtg    13260
gtgggaaact gggcgtagct tgtggtggcc gttggcgatt ggcatcctgg ggatcgctgt    13320
gctggtaggc agcttcgtcg cgaacaggtt ctaccagagc ggccacctgg ccgagtgcct    13380
actggtcacg acgtatctgc tgatcgcaac cgccgcagcg ctggccgtgc cgttgccgcg    13440
cggggtcaac tcgttgggggg cgccacaagt tgccggcgcc gctacggccg tgctgttttt    13500
gaccttgatg acgcggggcg gccctcggaa gcgtcatgag ttggcgtcgt ttgccgtgat    13560
caccgctatc gcggtcatcg cggccgccgc tgccttcggc tatggatacc aggactgggt    13620
ccccgcgggg gggatcgcat tcgggctgtt cattgtgacg aatgcggcca agctgaccgt    13680
cgcggtcgcg cggatcgcgc tgccgccgat tccggtaccc ggcgaaaccg tggcaacga     13740 ggagttgctc gatcccgtcg cgaccccgga ggctaccagc gaagaaaccc cgacctgca     13800 ggccatcatc gcgtcggtgc ccgcgtccgc ggtccggctc accgagcgca gcaaactggc    13860
caagcaactt ctgatcggat acgtcacgtc gggcaccctg attctggctg ccggtgccat    13920
cgcggtcgtg gtgcgcgggc acttctttgt acacagcctg gtggtcgcgg gtttgatcac    13980
gaccgtctgc ggatttcgct cgcggcttta cgccgagcgc tggtgtgcgt gggcgttgct    14040
ggcggcgacg gtcgcgattc cgacgggtct gacggccaaa ctcatcatct ggtacccgca    14100
```

```
ctatgcctgg ctgttgttga gcgtctacct cacggtagcc ctggttgcgc tcgtggtggt    14160
cgggtcgatg gctcacgtcc ggcgcgtttc accggtcgta aaacgaactc tggaattgat    14220
cgacggcgcc atgatcgctg ccatcattcc catgctgctg tggatcaccg ggtgtacga    14280 cacggtccgc aatatccggt tctgagccgg atcggctgat tggcggttcc tgacagaaca    14340
tcgaggacac ggcgcaggtt tgcatacctt cggcgcccga caaattgctg cgattgagcg    14400
tgtggcgcgt ccggtaaaat ttgctcgatg gggaacacgt ataggagatc cggcaatggc    14460
tgaaccgttg gccgtcgatc ccaccggctt gagcgcagcg gccgcgaaat tggccggcct    14520 cgttttccg cagcctccgg cgccgatcgc ggtcagcgga acggattcgg tggtagcagc    14580
aatcaacgag accatgccaa gcatcgaatc gctggtcagt gacgggctgc ccggcgtgaa    14640
agccgccctg actcgaacag catccaacat gaacgcggcg gcggacgtct atgcgaagac    14700
cgatcagtca ctgggaacca gtttgagcca gtatgcattc ggctcgtcgg gcgaaggcct    14760
ggctggcgtc gcctcggtcg gtggtcagcc aagtcaggct acccagctgc tgagcacacc    14820
cgtgtcacag gtcacgaccc agctcggcga cggccgct gagctggcac cccgtgttgt    14880
tgcgacggtg ccgcaactcg ttcagctggc tccgcacgcc gttcagatgt cgcaaaacgc    14940
atcccccatc gctcagacga tcagtcaaac cgcccaacag gccgcccaga gcgcgcaggg    15000
cggcagcggc ccaatgcccg cacagcttgc cagcgctgaa aaaccggcca ccgagcaagc    15060
ggagccggtc cacgaagtga caaacgacga tcagggcgac cagggcgacg tgcagccggc    15120
cgaggtcgtt gccgcggcac gtgacgaagg cgccggcgca tcaccgggcc agcagcccgg    15180 cggggggcgtt cccgcgcaag ccatggatac cggagccggt gcccgcccag cggcgagtcc    15240
gctggcggcc cccgtcgatc cgtcgactcc ggcaccctca acaaccacaa cgttgtagac    15300
cgggcctgcc agcggctccg tctcgcacgc agcgcctgtt gctgtcctgg cctcgtcagc    15360
atgcggcggc cagggcccgg tcgagcaacc cggtgacgta ttgccagtac agccagtccg    15420
cgacggccac acgctggacg gccgcgtcag tcgcagtgtg cgcttggtgc agggcaatct    15480
cctgtgagtg ggcagcgtag gcccggaacg cccgcagatg agcggcctcg cggcggtag    15540 cggtgctggt catgggcttc atcagctcga accacagcat gtgccgctca tcgcccggtg    15600
gattgacatc caccggcgcc ggcggcaaca agtcgagcaa acgctgatcg gtagtgtcgg    15660
ccagctgagc cgccgccgag gggtcgacga cctccagccg cgaccggccc gtcatttgc    15720 cgctctccgg aatgtcatct ggctccagca caatcttggc cacaccggga tccgaactgg    15780
ccaactgctc cgcggtaccg atcaccgccc gcagcgtcat gtcgtggaaa gccgcccagg    15840
cttgcacggc caaaaccggg taggtggcac agcgtgcaat ttcgtcaacc gggattgcgt    15900
gatccgcgct ggccaagtac accttattcg gcaattccat cccgtcgggt atgtaggcca    15960
gcccatagct gttggccacg acgatggaac cgtcggtggt caccgcggtg atccagaaga    16020
acccgtagtc gcccgcgttg ttgtcggacg cgttgagcgc cgccgcgatg cgtcgcgcca    16080
accgcagcgc atcaccgcgg ccacgctggc gggcgctggc agctcagtg gcggcgtcgc    16140 gtgccgcccg agccgccgac accgggatca tcgacaccgg cgtaccgtca tctgcagact    16200
cgctgcgatc gggtttgtcg atgtgatcgg tcgacggcgg gcgggcagga ggtgccgtcc    16260
gcgccgaggc cgcccgcgtg ctcggtgccg ccgccttgtc cgaggtagcc accgcgccc    16320 gcccagtggc agcatgcgac cccgcgcccg aggccgcggc cgtacccacg ctcgaacgcg    16380
cgcccgctcc cacggcggta ccgctcgcgc ggcggccgc cgcccgtgcg cccggacac    16440 cggacgccgc agccggcgtc accgacgcgg cggattcgtc cgcatgggca ggccccgact    16500
```

```
gcgtccccc  gcccgcatgc  tggcccggca  caccaggttg  ctccgccaac  gccgcgggtt    16560
tgacgtgcgg  cgccggctcg  cccctgggg   tgccggtgt   tgctggacca  gacggaccgg    16620
gagtggccgg  tgtaaccggc  tggggcccag  gcgatggcgc  cggtgccgga  gccggctgcg    16680
ggtgtggagc  gggagctggg  gtaacgggcg  tggccggggt  tgccggtgtg  gccggggcga    16740
ccgggggggt  gaccggcgtg  atcggggttg  gctcgcctgg  tgtgcccggt  ttgaccgggg    16800
tcaccggggt  gaccggcttg  cccggggtca  ccggcgtgac  gggagtgccg  ggcgttggtg    16860
tgatcggagt  taccgcgct   cccgggatgg  gtgtgattgg  ggttcccggg  gtgatcgggg    16920
ttcccggggt  gatcggggtt  cccggtgtgc  cggtgtgcc   cggggatggc  acgaccaggg    16980
taggcacgtc  tggggtggc   ggcgacttct  gctgaagcaa  atcctcgagt  gcgttcttcg    17040
gaggtttcca  attcttggat  tccagcaccc  gctcagcggt  ctcggcgacc  agactgacat    17100 tggcccatg   cgtcgccgtg  accaatgaat  tgatggcggt  atggcgctca  tcagcatcca    17160
ggctagggtc  attctccagg  atatcgatct  cccgttgagc  gccatccaca  ttattgccga    17220
tatcggattt  agcttgctca  atcaacccgg  caatatgcct  gtgccaggta  atcaccgtgg    17280
cgagataatc  ctgcagcgtc  atcaattgat  tgatgtttgc  acccagggcg  ccgttggcag    17340
cattggcggc  gccgccggac  cataggccgc  cttcgaagac  gtggccttc   tgctggcggc    17400 aggtgtccaa  tacatcggtg  accctttgca  aaacctggct  atattcctgg  gcccggtcat    17460
agaaagtgtc  ttcatcggct  tccacccagc  cgcccggatc  cagcatctgt  ctggcatagc    17520
tgcccgtcgg  cctggtaata  ctcatcccct  actgccctcc  ccaaaccgcc  agatcgcctc    17580
gcggatcacc  gtccggttgg  cctccggcat  ttcacgccgg  ctcggccgct  ggatccaccc    17640
cgcgccggta  ttcgcagtaa  cccgttgaat  ccgcgcgcat  gatgcaccgc  ttgggcgatc    17700
agccgggtgg  tcacctcgct  tgcgctggcc  gcgctgtcgc  acggggcgct  cggtggtaac    17760
ggacgtcata  attaaccagc  gtaaccgaac  ctaagaccag  ctagctgcgg  caatattggc    17820
gaccaggact  atggcgccct  ccgaacccgg  ccgatccatg  tcaaaacatt  gacaatgcgt    17880
actcacgccg  tgtcgggcgc  gctgaatgac  cgcattgcgg  cgctcattcg  gtgcgtagtc    17940
gctaccaccg  caacaatggg  cttaggccat  tccttcgttc  atcgcgcggg  acatggccga    18000
taacgcagcg  gtcagctgct  cgcccgccgc  gtcgttatac  gcggacgccg  cggcctgcgc    18060
attgtgcagc  gcctcgttga  cccgctgagc  caccgcctcg  gcacccagct  tcttcagcaa    18120
accatcttcg  atgcgcaggc  cggtgagcca  ctggtgccca  ttgatcgtca  cttcgacggt    18180
ctcggcttcg  tcggtggcgc  ggaaggatcc  gttgttcatc  tgattgagcg  tcccgtctag    18240
ggccgactga  aaccgcgccg  ccagcgtcaa  cgcccgggcg  acatgcgggt  ccaattcgtc    18300
catgctcact  tcgactcctt  actgtcctgg  cgccgacggt  taccaatgac  ggcctcggtc    18360
catgcccgat  cctcggtgta  gagcgcctcg  tcttcctgct  gagaacccctt  ggacttggcg    18420 cccccttgtc  cctgatgcgc  ggcacccatc  ggcattccca  tgccaccgcc  gcccagcgcg    18480
gcgccgccgc  cggcccttcc  ctggcctaag  ccggcaatgt  caccagcgcc  agcgggccgc    18540
accgattcgg  cgccccgat   cgcggatccc  aacggcgccg  acggcacccc  gccgcctcca    18600
ccgccaccga  gcgatgccgc  tttgaccgcc  acgtcgcccg  acagcgctgc  ggcttcccgc    18660
ccagccgacg  tcagctgcgc  cgccgtgtca  gcgggaggc   caccacccgg  cgatccgta   18720 ggcggaacca  tcggtgcggc  tggcatcccg  gtaccgggag  tcacaccgga  gccgtcagac    18780
ggcggcatca  ggaagccagg  gatcaatccc  tgctcttgcg  gaggcggggg  cgggtcgatc    18840
ttgatggcgg  ggggaggctt  cggcgggttt  accggttcca  gggctgcctt  gttgttgtat    18900
```

```
tcggtcagca ccttctccga cctctgctga tactccgcgt acaccgggag aatttggtcg   18960
cgggccgaag ggttttccgc gtaaagccgt tcgagcccga ctatgtcttc ataagtcgga   19020
tgttcccgcc tagcccacac gtgcagctgc gcgacatatt gagcctgctt ggccatcgca   19080
gcgctcaatt tggccatgtg gagtatccat tgccgttgtt gatcgagcga agcctcgcaa   19140
gcggtagccg catcgccttc ccagttgtca aaccccggga accgcttgac gtcgccttgc   19200
agcgtcaggt tgaaagtgtt ccacccatcc gcaaagtgcg cgagcgatgc gccttggtcg   19260
cccgtttcga gcttccttgc cgcttctttg agatccatga agttgggttc accggccgtg   19320
gccaccctcg gcgtatcggt tagttcggcc gaactgtccc ctccgacggc cccggccgat   19380
tctgcctgca cagttccttc gccgtcgttg tccagcgcgg tcgcagcctc ctcatcaacc   19440
tcgccatacg ccttggccgc gttgcgcagc gaggtcgcca gacgctgccg ctctttggca   19500
ccggccgcca ggtattcccg catgttgtcg gcggacaata ccagctgttg ggcggcgttt   19560
ttagccgccg tgagttcgca cggtgtgatg gggacatcag tcggtgggtc cgccatcggg   19620
gcctccacct cgttggccct gttcaaaatc tcttgctgat ccaccgtcac ggtctgcgac   19680
tgcgtcatat cggatcatcc tccttagtgc tatagccatt atcgtcgcta aactgaaagg   19740
ttcctgcact aatttgatgc cgcccgttca tgccggcatc gcgaacggat cgccctactt   19800
cggcagcgcc atctggtagc ggcttttcctc gggtggggaa accggcgaa tcggcagctg   19860 ccgatgccgc ggggtaccga tcacattgtg ccgcagaatc accggtcaa taccgggatg   19920 cgggccgaga taggtcgtcg cattcggcca cgccacctt acctcctgcc cgatgtgtgc   19980
gccgatcaac cgggcaaatt cctcgaactg tgggcccgact gtgaccatcg cacctgccgc   20040
cgccgcacgc accacgaact gggtgaatgt ctgagcgtca cccaggttga gggcgatgtc   20100
gacatcgtcg aagggcatgt agaccgggca tcggttcacc gtctcgccga ccagtacccc   20160
agctgacccg atcggcagct ggcagtggcg gttggccacc agatgctggc cttgcagcgc   20220
gggccgctgc ccgccaaata ggcgggcgaa gcccctgggt gtcttgggct tgtccgccgt   20280
ggtcagcaac accgtggact gcggggccat cccccggcgcg acccggactc tggtgatggt   20340
gtggtccgcg cgcgccgacc accatacatc cggacctccg ggcgccgcgt aggcggcagt   20400
gtaggcatcg cgcccctttga tcatcgacca tttctcccgc acaaagccga tgtcggtggc   20460
gtggtcgtag tcatcgaagc tgcggccaca caccgcgtcg acaccatggc tagccagtcg   20520
atcggcaatg cgcgtcgcgg acgccaccaa ataccgggcc agtcctgcga cgccttcatc   20580
gcggcgctgc gccgatttgc gggtgcgttc cgggtcggcg cgcagcacga tccaggtccg   20640
gcggttcgcc ggcgccgggt ctgtcccgat cacctgctga tacagactca ccacgtccgg   20700
cgctgcggta ttgccgacgc ggtagccggc tgagacgata tcggcctcca agtcgggaca   20760
gtgcaccgac aggagctcct ccaccagtcc ggtgtccagc atgtcgtcgg tgtgggcttg   20820
cccgtcgacg atgaccgtcg gcgtgaatgg tcggggaatg agctcgatta cggcgaccag   20880
aaactcgcct tgccagcgca ccgcaacgtg atctcctggc ttcacggtgg ccccgaccac   20940
aggttctgac gaggaatccg ggggccgtcg gcgccgccgc aaccacgcgt acaccgcgc    21000 cacccagccg gtgatccggc ggccgtagaa agtgaccgtg gccacgatga cgcccaacga   21060
ggccagcgca atccccgccc accagtagcg cgtctccaag aatgcgatga tgcatggcgg   21120
ggccaacgcg gaggcaagca aggcgtgccc ggtgctgaac cgcagcccta aaggatttct   21180
catcggcggc tcagcgcccg tctagccagc gcgcccaggc ccagggccaa cgtaaggccg   21240
acggccacca acgccacagc cgtaatcggg cgacgatcgg gacccggctc caccaccggg   21300
```

```
ggtggaagtc gtctgacgtt gtatggcgcc gaagcagggc cgggcggaat gtcccacgtc   21360
agcgcggcca ccgcatcgat gacgccggcg ccgaccaggt cgtcgacccc gcccccgggg   21420
tgtctcgcgg tggcggtgat ccggtggatg atctgcgccg gcgtcaggtc ggggaaccgc   21480
tgccgaagca gggccgccag acccgacaca tatgccgcgg caaacgaggt gccggcgatg   21540
ggtaccggcc cctcccggcc ttgcagcgca ttcaccggtt caccggtgtc gccgagcgcg   21600
acgatgtttt ctgcgggcgc ggccacgtcc acccacggtc cgtgcatcga aacgagctg    21660 ggcatcccgg tctggccgat accgccgacg cttaacacca gcggtgcgta ccacgccggg   21720
gtgacaacgg tctgcacatt gttccagccg cgtgggtcgc cgggtgtgga cgggtccggc   21780
gccggattct gtacgcaatc gccaccggtg ttgccggccg cgaccaccac caccacgcct   21840
ttgacgttga ccgcatagtc gatggatgca cccagtgagg tttcatcgat cggcctgctc   21900
accttgtagc aggcggcttc actgatgttg atcacaccca cgccgaggtt ggcggcgtgc   21960
accacggcgc gggcaagact gcggatggaa ccggcggccg gggtggcgtt ggggtcattc   22020
gggttggctt gtgagccgac cggttcgaag gcctcagacg tctgacgtag cgagagcagt   22080
cgagcgtcgg gcgcgacgcc gacgaacccg tcggtgggcg cgggccggcc cgcgatgatg   22140
gatgctgtga gagtcccatg ggcatcacag tcagacaggc cgttaccggc ctggtcgacg   22200
aaatcgccgc caggttccgc cgggacccgt ggcgaagcgt cgacaccggt gtcgatcacc   22260
gccaccgtca ccccggcccc ggtcgcgaac ttgtgggcat cggccacgcc cagatacgtg   22320
ttgctccacg gcggatcgtg aaccccgac cccggcagca tggtgggcga cgcgcacaaa   22380
acgcgctgtt cggtaggctg atccgggccc gtcacgtcgg gcggcaacgc gcccggatcg   22440
atcggcggtg gcgtgatggc cgatgcgggc gacgcgtga gcaacgccag cgccaccgtg    22500
atcagaaaga tacggtgcac tcccagaaca ctccattcgt tgagattcat tgcgattcat   22560
tgagctgcgt tgctaccttg ggccacttga cggacctgtg tgcattttag acgtaacggc   22620
tgggcaaaca acgctgtcac gcctgggctg gtccgccgcg ccgaccaggg cgcgtaggcg   22680
ctgtacctgg accacgccgg gactcaacgg ttttgctacc gcactagccg atatgcggct   22740
gctaccaaac gatcgcggcc atgtctcggt tgtctgagca cacgctgcgt atcgcggcat   22800
cgatgtcggt ggcggtgatg atctgcagat cctgaaccga taccggttgg cccgcacgtt   22860
tttgcgcaac caccgggtg tcccggaacc cttcggcgcg ttcgatcacg ttgcgggcga    22920
accgaccgtt ttgcatagcg tcgataccgt gctgcccact aggggtggtg tagttacgga   22980
tggtggtgac cgcgtcgagg aatacctccc gtgcggcgtc atcgagctgg ctggcgcgcg   23040
gtgtagcgta gcggtgtcca atctcgacga tctccaccgg cgaataagac tcgaaccgca   23100
gctttcggtt gaaccggcca gccaaacccg ggttcacggt gaggaattca tccacctgat   23160
cctcatagcc ggccccgatg aaacagaagt cgaatcggtg tgtttccaat gaaccagga    23220 gttgattgac cgcctccatg ccgatcatgt ccggtgttcc gtcttgatga cgttcgatca   23280
gcgagtagaa ctcgtccatg aaaatgattc gcccgagtga cttttcgatc agctcgttcg   23340
tcttgggtcc tgactcccg atgtagtgcc cacagaagtc cgatcggcga acttctcgaa    23400
tttcggggtg acgcacgatc cccatgccgg cgtagatctt gccgagcgct tcagcggtgg   23460
ttgtcttacc tgtgcctggt ggccccacca gcaacatgtg gttggtctgc ccctccaccg   23520
gtaggccgtg ctctaggcgc atcatgcgca cctcgagttg gtcttccagc gccgataccg   23580
cttgcttgac cgccgccagg cccacctgtt tggccagcag ttcccggccc tcggctagca   23640
gctcgccgcg ccgctgcgct gcattgtcgt catcgagctg gtcgcggctt ttcgccgtcg   23700
```

```
aagcatccca acggtcggag cggctggcga tggttcgttc atcggtaaca atcaagcgca    23760
ggttcgggtc cgccagggct tctttggcgg cgtcggtgag caccccgttg atggtggcct    23820
tcgacagcca gatctgggcc ttgtcctcct catgcagttg ccggtacacc atcccccgca    23880
catacgccaa gtcggcgacc agcagcggaa tatcggccgg tccgatcgcc gcggtgagca    23940
cgtcggcgcc gaaccgctcc gatgacctgc tgtgtccgat cacgtccacc cggtccagcc    24000
agtccagggc cactcgcccc tgcccgagat gggcggcggc gtgggctgcc agcgcacaaa    24060
tcgacgcggt caccgccggc atgacgatcg cctgtggcgg cagatcctcg gcggccgtcg    24120
acaacacgtc gggccatcgc tgcgtgacgt acatcaggaa cgcccgagcc agctgatgcc    24180
actggtagtt gcgccacgaa tccaatagct cgcggtttgc taacagggca tcggccttcg    24240
catactcccc cgcgatcgtc aacgccgacg acagcgccag ccccacctga gatgcgtcgg    24300
tcaccgtgat cccgatggat ggtcccagct ggacctcagc ggccaacgtc cggccgatcc    24360
gcgtggtctc gcggtgcagc cactcgctat gggcgttgag ctgcttaagc gaggccagat    24420
cgcggtcacc gcaggcgata cgacccagcc acgcgtcggc catcgacgga tcggcctcgg    24480
tggcagccac aaactcaggc aacgccgcca cgcatccctg gccattcttg atcgtcatcg    24540
cccgatcgaa atgccggcgc gcagtgagta aatcacccat cgtgtccacc attctcgaca    24600
tcgccgccgc tgtcaccgcg gttgcaacgt gtgtctgtca ctctgtgcct caaattccgt    24660
tggcaacgtt ctaccggcct atcgacatcg tgaccggctc aaggctgaca tagcggttct    24720
ccgcacggaa catttccatc tcaaccagcc agttttgtcc tgccgcaccg actttcaccg    24780
ttgcccgatc gatttgttcg atggtcacct cgaagccatg ccgatcgctc tcggacagcg    24840
aggtaccggg tcgggcaatg gtgatgacac tggctggccg tggcgtgggc gaaatcgcga    24900
catcgacacc gctgccttca gatttgccgt catcgccgtt cttgcgccgc cgcacgtact    24960
ccacgacgcc gacagtggtg cgcggcgcgg gccgtggtgt gccgacgatg ctcaactgcg    25020
gcatgcgtac gctggcccaa cgctcttggt cgcgagtgtg cacacacacc cgctcaccgg    25080
caccgacgac gcgaatacg atcctcttgg cgatcgtgtc gtccgcggcc acgaagacgc    25140
gcgacagctc accggcgtcg gtaacgggaa tcatcagccg gtccccgttg ctcagcttgc    25200
caatcaacac ccccgacggt ccgatctcgg tgactagctg cgccggcaac gggcagcgcc    25260
gctgtccgcg taggtgtgga cgtggcccgc acatgttggc cgcagccgcg gcggcttgct    25320
caccattgag ccgacgcaag atcacactgg gcggggtagg cgccggcgtc ggtgtgcgca    25380
cggtgatggt cgcggtgcac gtcgcgtccg gatacaccgt tacgttctgg atgacctcat    25440
cggcacgcag cgtccaggct tgcgagagaa cccgcgacga aatcgcctca gccgggtacg    25500
catacgtcgt catccacccg gcttcaccgc ggatagcttt ccagcgctgc gcactcccgg    25560
ctaccgcgtc cgaccccagc cggcgatcaa gctcagccaa gtctgttgcg gtggccagtt    25620
tggcgcgcaa gccctgacag cgcagggagc tggcaacgcg ttgggcgacc gaaatggcag    25680
cggccccaac gctggtacgc cagcgtaaag cttgggtgtt gccgatcacc ggaagccgca    25740
tgatcagcca cgtttcgcgc cgcccggcat acggcggcgt accgatctcc gcgtcataca    25800
cccgcgggta atcgccgacg gtgccggttc gcgagccgaa ggtgacgacg ctgattgaat    25860
cgagttccag gtccagcggg tggcgcagca acggcgcgag ctcaacgacg tcaatcacgt    25920
tgtcgctttc tacggtcacc gacccggtga ccgtagtcgc ccggtgcgct cggccgagaa    25980
gttgcaccgc caccaccgcg acaccgtctt gcacgcggac gccaccccg gatcggttgt    26040 tggccaaggt aattgggtca ttccatttga cgggacgccg accccgcagc cccagtaccg    26100
```

```
cccacgacca cgccggctga ccccaccact gtacgaacac caaggcgacg ccgaccacga      26160
cagccatgac cgcacctagc tggccgccca gcgcccagcc cgccgacgcg agcacgaaca      26220
ctgtccacac cccggcgacc cgcctcgcac tgcgcgggct gaacccggtc agcttggacg      26280
tcaacgcgcc ctccgtagcc gagccccgat tgccattgcc agcacaccgg tggccactgc      26340
gccgacgaac ccgatagcga tattgcgcgc ccggtgatc                            26379
```

<210> SEQ ID NO 66
<211> LENGTH: 288
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 66

```
atgacagagc agcagtggaa tttcgcgggt atcgaggccg cggcaagcgc aatccaggga       60
aatgtcacgt ccattcattc cctccttgac gaggggaagc agtccctgac caagctcgca      120
gcggcctggg gcgtagcgg ttcggaggcg taccagggtg tccagcaaaa atggacgcc       180 acggctaccg agctgaacaa cgcgctgcag aacctggcgc ggacgatcag cgaagccggt      240
caggcaatgg cttcgaccga aggcaaccgt acgggatgt tcgcatag                    288
```

<210> SEQ ID NO 67
<211> LENGTH: 444
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 67

```
cgacgaggag cagcagcagg cgctgtcctc gcaaatgggc ttctgacccg ctaatacgaa       60
aagaaacgga gcaaaaacat gacagagcag cagtggaatt tcgcgggtat cgaggccgcg      120
gcaagcgcaa tccagggaaa tgtcacgtcc attcattccc tccttgacga ggggaagcag      180
tccctgacca agctcgcagc ggcctggggc ggtagcggtt cggaggcgta ccagggtgtc      240
cagcaaaaat ggcaggccac ggctaccgag ctgaacaacg cgctgcagaa cctggcgcgg      300
acgatcagcg aagccggtca ggcaatggct tcgaccgaag gcaacgtcac tgggatgttc      360
gactagggca cgccgagtt cgcgtagaat agcgaaacac gggatcgggc gagttcgacc      420
ttccgtcggt ctcgcccttt ctcg                                             444
```

<210> SEQ ID NO 68
<211> LENGTH: 56
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1)..(33)

<400> SEQUENCE: 68

```
act ggg atg ttc gca cat cat cat cat cat cac tacactagtg gcaacgccga       53
Thr Gly Met Phe Ala His His His His His His
  1               5                  10 gtt                                                                     56
```

```
<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 69

Thr Gly Met Phe Ala His His His His His His
 1               5                   10

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

His His His His His His
 1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

His His His His His
 1               5

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Phe Leu Asn Cys Cys Pro Gly Cys Cys Met Glu Pro
 1               5                   10

<210> SEQ ID NO 73
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Tyr Lys Asp Asp Asp Asp Lys
 1               5
```